US007569374B2

(12) United States Patent
Graham et al.

(10) Patent No.: US 7,569,374 B2
(45) Date of Patent: Aug. 4, 2009

(54) HCV RNA-DEPENDENT RNA POLYMERASE

(75) Inventors: Donald J. Graham, Green Lane, PA (US); Amy L. Simcoe, Collegeville, PA (US); Steven W. Ludmerer, North Wales, PA (US); Osvaldo A. Flores, North Wales, PA (US); Robert L. LaFemina, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 12/002,392

(22) Filed: Dec. 17, 2007

(65) Prior Publication Data
US 2008/0187903 A1 Aug. 7, 2008

Related U.S. Application Data

(62) Division of application No. 10/584,810, filed as application No. PCT/US2005/000292 on Jan. 6, 2005, now Pat. No. 7,329,732.

(60) Provisional application No. 60/535,708, filed on Jan. 9, 2004.

(51) Int. Cl.
*C12N 9/00* (2006.01)
*C07K 14/08* (2006.01)
*G01N 33/53* (2006.01)
*C12P 21/00* (2006.01)

(52) U.S. Cl. ............ 435/183; 435/7.6; 435/69.1; 530/350

(58) Field of Classification Search ............... None
See application file for complete search history.

(56) References Cited

U.S. PATENT DOCUMENTS 6,248,589 B1 * 6/2001 Hagedorn et al. .......... 435/471
2003/0236251 A1 12/2003 Beaulieu

FOREIGN PATENT DOCUMENTS

| WO | WO96/37619 | 11/1996 |
| WO | WO99/51781 | 10/1999 |
| WO | WO 2005/012502 | * 2/2005 |

OTHER PUBLICATIONS

GenPept BAA01761, "polyprotein precursor [Hepatitis C virus]," May 1992.*
Dhanak et al. "Identification and Biological Characterization of Heterocyclic Inhibitors of the Hepatitis C Virus RNA-dependent RNA Polymerase," Journal of Biological Chemistry, vol. 277 No. 41, pp. 38322-38327 (2002).*
Sakamoto et al., "Entire nucleotide sequence and characterization of a hepatitis C virus of genotype V/3a," Journal of General Virology, vol. 75 No. 7, pp. 1761-1768 (Jul. 1994).*
GenPept BAA04609, "polyprotein" (Feb. 1996).*
NCBI, AF177036 Hepatitis C virus . . . [gi:6010579] Oct. 5, 1999.
NCBI, P26661 Genome polyprotein [gi: 130468] Jun. 15, 20002.
NCBI, D17763 Hepatitis C Virus [gi: 514395] Feb. 4, 1999.

Bartenschlager et al. 'Nonstructural Protein 3 of the Hepatitis C Virus . . . at the NS3/4 and NS4/5 Junctions', Journal of Virology, vol. 67, No. 7, pp. 3835-3844 Jul. 1993.
Beaulieu, et al. 'Non-Nucleoside Inhibitors of the Hepatitis C Virus NS5B . . . Benzimidazole Derivatives', Bioorganic & Medicinal Chemistry Letters, vol. 14 pp. 119-124 (2004).
Behrens et al. Identification and Properties of the RNA-Dependent RNA Polymerase of Hepatitis C Virus, EMBO, vol. 15, No. 1, pp. 12-22 (1996).
Carroll, et al.. 'Inhibition of Hepatitis C Virus RNA Replication by 2'-Modified Nucleoside Analogs', Journal of Biological Chemistry, vol. 278, No. 14, Issue of Apr. 4, pp. 11979-11984 (2003).
Choo et al., 'Isolation of a cDNA Clone Derived from a Blood-Borne Non-A, Non-B Viral Hepatitis Genome', Science, vol. 244pp. 359-361, (Apr. 1989).
De Francesco et al. 'RNA-Dependent RNA Polymerase of Hepatitis C Virus', Methods in Enzymology, vol. 275, pp. 58-67.
Farci et al. 'Clinical Significance of Hepatitis C Virus Genotypes and Quasispecies', Seminars in Liver Disease, vol. 20, No. 1, pp. 103-125 (2000).
Ferrari, et al. 'Characterization of Soluble Hepatitis C Virus RNA-Dependent RNA Polymerase Expressed in *Escherichia coli*', Journal of Virology, vol. 73, No. 2, pp. 1649-1654 (Feb. 1999).
Grakoui, et al. 'A Second Hepatitis C Virus-Encoded Proteinase', Proc. Natl. Sci. USA, vol. 90, pp. 10583-10587 (Nov. 1993).
Huikata, et al. Proteolytic Processing and Membrane Association of Putattive Nonstructural Proteins of Hepatitis C Virus, vol. 90, pp. 10773-10777 (Nov. 1993).
Kolykhalov et al. 'Transmission of Hepatitis C by Intrahepatic Inoculation with Transcribed RNA', Science, vol. 277 pp. 570-574, (Jul. 25, 1997).
Kuo et al., 'An Assay for Cirulating Antibodies to a Major Etiologic Virus of Human Non-A, Non-B Hepatitis', Science, vol. 244, pp. 362-364 (1989).
Leveque et al. 'Identification of a C-Terminal Regulatory Motif in Hepatitis C Virus RNA-Dependent RNA Polymerase: Structural and Biochemical Analysis', Journal of Virology, vol. 77, No. 16, pp. 9020-9028 (Aug. 2003).
Lohmann et al. 'Biochemical and Kinetic Analyses of NSB RNA-Dependent RNA Polymerase of the Hepatitis C Virus', Virology, vol. 249, pp. 108-118 (1998).
Luo et al. 'De Novo Initiation of RNA Synthesis by the RNA-Dependent RNA Polymerase (NS5B) of Hepatits B Virus', Journal of Virology, vol. 74, No. 2, pp. 851-863 (Jan. 2000).
Migliaccio et al. 'Characterization of Resistance to Non-Obligate Chain-Terminating Ribonucleoside Analogs that Inhibit Hepatitis C Virus Replicaiton in Vitro', Journal of Biological Chemistry, vol. 278, No. 49, Issue of Dec. 5, pp. 49164-49170 (2003).

(Continued)

*Primary Examiner*—Zachariah Lucas
(74) *Attorney, Agent, or Firm*—Melissa B. Wenk; Sheldon O. Heber

(57) ABSTRACT

The present invention features NS5B polypeptides from different clinically important HCV genotypes. The polypeptides can be used individually, or as part of a panel of RNA-dependent RNA polymerases, to evaluate the effectiveness of a compound to inhibit NS5B activity.

2 Claims, 5 Drawing Sheets

OTHER PUBLICATIONS

Mizushima et al. 'Analysis of N-Terminal Processing of Hepatitis C Virus Nonstructural Protein 2', Journal of Virology, vol. 68, No. 4 pp. 2731-2734 (Apr. 1994).

Oh, et al. 'A Recombinant Hepatitis C Virus RNA-Dependent RNA Polymerase Capable of Copying the Full-Length Viral RNA', Journal of Virology, vol. 73, No. 9, pp. 7694-7702 (Sep. 1999).

Okamoto et al. 'Full-length Sequence of a Hepatitis C Virus Genome Having Poor Homology . . . of Four Distinct Genotypes', Virology, vol. 188, pp. 331-341 (1992).

Regenmortel et al. Seventh Report of the International Committee on Taxonomy of Viruses; Virus Taxonomy—Classification and Nomenclature of Viruses, Academic Press, p. 876 (2000).

Sakamoto et al. Entire Nucleotide Seuence and Characterization of a Hepatitis C Viirus of Genotype V/3a, Journal of General Virology, vol. 75, Pt 7, pp. 1761-1768 (1994).

Shim et al. 'Canonical 3'-deoxyribonucleotides as a Chain Terminator for HCV NS5B RNA-dependent RNA Polymerase', Antiviral Research, vol. 58, pp. 243-251 (2003).

Takamizawa et al. 'Structure and Organization of the Hepatitis C Virus Genome Isolated from Human Carriers', Journal of Virology, vol. 65, No. 3, pp. 1105-1113 (Mar. 1991).

Tomei, et al. 'NS3 Is a Serine Protease Required for Processing of Hepatitis C Virus Polyprotein', Journal of Virology, vol. 67, No. 7, pp. 4017-4026 (Jul. 1993).

Walker et al. 'HCV RNA-dependent RNA Polymerase as a Target for Antiviral Development', Current Opinion in Pharmacology, vol. 2, pp. 1-7 (2002).

Yamashita et al. 'RNA-dependent RNA Polymerase Actiivty of the Soluble Recombinant . . . C-terminal Region', Journal of Biological Chemistry, vol. 273, No. 25, Issue of Jun. 19, pp. 15479-15486 (1998).

Yanagi, et al. 'Transcripts from a Single Full-length cDNA Clone of Hepatitis C Virus . . . the Liver of a Chimpanzee', Proc. Natl. Acad. Sci. USA, vol. 94, pp. 8737-8743 (Aug. 1997).

Yanagi, et al. 'Hepatitis C Virus: An infectious Molecular Clone of a Second Major Genotype (2a) and Lack of Viability of Intertypic 1a and 2a Chimeras', Virology, vol. 262, pp. 250-263 (1999).

Lohmann et al., "Biochemical Properties of Hepatitis C virus NS5B RNA-dependent RNA Polymerase and Identification of Amino Acid Sequence Motifs Essential for Enzymatic Activity," Journal of Virology, vol. 71 No. 11, pp. 8416-8428 (Nov. 1997).

GenBank Accession Z97730, "Hepatitis C Virus NS5b Gene," Oct. 1997.

* cited by examiner

MSMSYTWTGALITPCSPEEEKLPINPLSNSLLRYHNKVYCTTTKSASLRAKKVTFDRMQVLDSYYDSVLKDIKL
AASKVTARLLTMEEACQLTPPHSARSKYGFGAKEVRSLSGRAVNHIKSVWKDLLEDSETPIPTTIMAKNEVFCV
DPTKGGKKAARLIVYPDLGVRVCEKMALYDITQKLPQAVMGASYGFQYSPAQRVEFLLKAWAEKKDPMGFSYDT
RCFDSTVTERDIRTEESIYRACSLPEEAHTAIHSLTERLYVGGPMFNSKGQTCGYRRCRASGVLTTSMGNTITC
YVKALAACKAAGIIAPTMLVCGDDLVVISESQGTEEDERNLRAFTEAMTRYSAPPGDPPRPEYDLELITSCSSN
VSVALGPQGRRRYYLTRDPTTPIARAAWETVRHSPVNSWLGNIIQYAPTIWARMVLMTHFFSILMAQDTLDQNL
NFEMYGAVYSVSPLDLPAIIERLHGLDAFSLHTYTPHELTRVASALRKLGAPPLRAWKSRARAVRASLISRGGR
AAVCGRYLFNWAVKTKLKLTPLPEARLLDLSSWFTVGAGGGDIYHSVSRARPR

FIG. 1A

MSMSYTWTGALITPCGPEEEKLPINPLSNSLMRFHNKVYSTTSRSASLRAKKVTFDRVQVLDAHYDSVLQDVKR
AASKVSARLLTVEEACALTPPHSAKSRYGFGAKEVRSLSRRAVNHIRSVWEDLLEDQHTPIDTTIMAKNEVFCI
DPTKGGKKPARLIVYPDLGVRVCEKMALYDIAQKLPKAIMGPSYGFQYSPAERVDFLLKAWGSKKDPMGFSYDT
RCFDSTVTERDIRTEESIYQACSLPQEARTVIHSLTERLYVGGPMTNSKGQSCGYRRCRASGVFTTSMGNTMTC
YIKALAACKAAGIVDPVMLVCGDDLVVISESQGNEEDERNLRAFTEAMTRYSAPPGDLPRPEYDLELITSCSSN
VSVALDSRGRRRYFLTRDPTTPITRAAWETVRHSPVNSWLGNIIQYAPTIWVRMVIMTHFFSILLAQDTLNQNL
NFEMYGAVYSVNPLDLPAIIERLHGLEAFSLHTYSPHELSRVAATLRKLGAPPLRAWKSRARAVRASLIAQGAR
AAICGRYLFNWAVKTKLKLTPLPEASRLDLSGWFTVGAGGGDIYHSVSHARPR

FIG. 1B

MSMSYTWTGALITPCSAEEEKLPISPLSNSLLRHHNLVYSTSSRSASQRQRKVTFDRLQVLDDHYKTALKEVKE
RASRVKARMLTIEEACALVPPHSARSKFGYSAKDVRSLSSRAIDQIRSVWEDLLEDTTTPIPTTIMAKNEVFCV
DPAKGGRKPARLIVYPDLGVRVCEKRALYDVIQKLSIETMGSAYGFQYSPQQRVERLLKMWTSKKTPLGFSYDT
RCFDSTVTEQDIRVEEEIYQCCNLEPEARKVISSLTERLYCGGPMFNSKGAQCGYRRCRASGVLPTSFGNTITC
YIKATAAAKAAGLRNPDFLVCGDDLVVVAESDGVDEDRAALRAFTEAMTRYSAPPGDAPQPTYDLELITSCSSN
VSVARDDKGRRYYYLTRDATTPLARAAWETARHTPVNSWLGNIIMYAPTIWVRMVMMTHFFSILQSQEILDRPL
DFEMYGATYSVTPLDLPAIIERLHGLSAFTLHSYSPVELNRVAGTLRKLGCPPLRAWRHRARAVRAKLIAQGGK
AKICGLYLFNWAVRTKTNLTPLPATGQLDLSSWFTVGVGGNDIYHSVSRARTR

FIG. 1C

MSMSYTWTGALVTPCAAEESKLPISPLSNSLLRHHNMVYATTTRSAVTRQKKVTFDRLQVVDSHYNEVLKEIKA
RASRVKARLLTTEEACDLTPPHSARSKFGYGAKDVRSHSRKAINHISSVWKDLLDDNNTPIPTTIMAKNEVFAV
NPAKGGRKPARLIVYPDLGVRVCEKRALHDVIKKLPEAVMGAAYGFQYSPAQRVEFLLTAWKSKKTPMGFSYDT
RCFDSTVTEKDIRVEEEVYQCCDLEPEARKVITALTDRLYVGGPMHNSKGDLCGYRRCRASGVYTTSFGNTLTC
YLKATAAIRAAGLRDCTMLVCGDDLVVIAESDGVEEDNRALRAFTEAMTRYSAPPGDAPQPAYDLELITSCSSN
VSVAHDVTGKKVYYLTRDPETPLARAAWETVRHTPVNSWLGNIIVYAPTIWVRMILMTHFFSILQSQEALEKAL
DFDMYGVTYSITPLDLPAIIQRLHGLSAFTLHGYSPHELNRVAGALRKLGVPPLRAWRHRARAVRAKLIAQGGR
AKICGIYLFNWAVKTKLKLTPLPAAAKLDLSGWFTVGAGGGDIYHSMSHARPR

FIG. 1D

MSMSYTWTGALITPCAAEEEKLPINPLSNSLIRHHNMVYSTTSRSASLRQKKVTFDRVQVFDQHYQEILKEIKL
RASKVQAKLLSVEEACDLTPSHSARSKYGYGAQDVRSHASKAVNHIRSVWEDLLEDSDTPIPTTIMAKNEVFCV
DPSKGGRKPARLIVYPDLGVRVCEKMALYDVTQKLPQAVMGSAYGFQYSPTQRVEYLLKMWRSKKVPMGFSYDT
RCFDSTVTERDIRTENDIYQSCQLDPVARRAVSSLTERLYVGGPMVNSKGQSCGYRRCRASGVLPTSMGNTITC
YLKAQAACRAANIKDCDMLVCGDDLVVICESAGVQEDTESLRAFTDAMTRYSAPPGDAPQPTYDLELITSCSSN
VSVAHDGNGKRYYYLTRDCTTPLARAAWETARHTPVNSWLGNIIMFAPTIWVRMVLMTHFFSILQSQEQLEKAL
DFDIYGVTYSVSPLDLPAIIQRLHGMAAFSLHGYSPVELNRVGACLRKLGVPPLRAWRHRARAVRAKLIAQGGK
AAICGKYLFNWAVKTKLKLTPLVSASKLDLSGWFVAGYDGGDIYHSVSQARPR

FIG. 1E

```
ATGTCAATGTCGTATACATGGACAGGCGCCTTGATCACTCCTTGTAGTCCCGAAGAGGAGAAGTTACCGATTAA
CCCCTTGAGCAACTCCCTGTTGCGATATCACAACAAGGTGTACTGTACCACAACAAAGAGCGCCTCACTAAGGG
CTAAAAAGGTAACTTTTGATAGGATGCAAGTGCTCGACTCCTACTACGACTCAGTCTTAAAGGACATTAAGCTA
GCGGCCTCCAAGGTCACCGCAAGGTCCTCACCATGGAGGAGGCTTGCCAGTTAACCCCACCCCATTCTGCAAG
ATCTAAATATGGGTTTGGGGCTAAGGAGGTCCGCAGCTTGTCCGGGAGGGCCGTTAACCACATCAAGTCCGTGT
GGAAGGACCTCCTGGAGGACTCAGAAACACCAATTCCCACAACCATTATGGCCAAAAATGAGGTGTTCTGCGTG
GACCCCACCAAGGGGGGCAAGAAAGCAGCTCGCCTTATCGTTTACCCTGACCTCGGCGTCAGGGTCTGCGAGAA
GATGGCCCTTTATGACATTACACAAAAACTTCCTCAGGCGGTGATGGGGGCTTCTTATGGATTCCAGTATTCCC
CCGCTCAGCGGGTAGAGTTTCTCTTGAAAGCATGGGCGGAAAAGAAGGACCCTATGGGTTTTTCGTATGATACC
CGATGCTTTGACTCAACCGTCACTGAGAGAGACATCAGGACTGAGGAGTCCATATATCGGGCCTGCTCCTTGCC
CGAGGAGGCCCACACTGCCATACACTCGCTAACTGAGAGACTTTACGTGGGAGGGCCTATGTTCAACAGCAAGG
GCCAAACCTGCGGGTACAGGCGTTGCCGCGCCAGCGGGTGCTCACCACTAGCATGGGGAACACCATCACATGC
TACGTGAAAGCCTTAGCGGCTTGTAAAGCTGCAGGGATAATCGCGCCCACAATGCTGGTATGCGGCGATGACTT
GGTTGTCATCTCAGAAAGCCAGGGGACCGAGGAGGACGAGCGGAACCTGAGAGCCTTCACGGAGGCTATGACCA
GGTATTCTGCCCCTCCTGGTGACCCCCCAGACCGGAGTATGATCTGGAGCTGATAACATCTTGCTCCTCAAAT
GTGTCTGTGGCGCTGGGCCCACAAGGCCGCCGCAGATACTACCTGACCAGAGACCCTACCACTCCAATCGCCCG
GGCTGCCTGGGAAACAGTTAGACACTCCCCTGTCAATTCATGGCTGGGAAACATCATCCAGTACGCCCCGACCA
TATGGGCTCGCATGGTCCTGATGACACACTTCTTCTCCATTCTCATGGCTCAAGACACGCTGGACCCAGAACCTC
AACTTTGAGATGTACGGAGCGGTGTACTCCGTGAGTCCCTTGGACCTCCCAGCTATAATTGAAAGGTTACATGG
GCTTGACGCTTTTTCTCTGCACACATACACTCCCCACGAACTGACACGGGTGGCTTCAGCCCTCAGAAAACTTG
GGGCGCCACCCCTCAGAGCGTGGAAGAGCCGGGCACGTGCAGTCAGGGCGTCCCTCATCTCCCGTGGGGGGAGA
GCGGCCGTCTGCGGTCGATATCTCTTCAACTGGGCGGTGAAGACCAAGCTCAAACTCACTCCATTGCCGGAGGC
GCGCCTCCTGGATTTATCCAGCTGGTTCACCGTCGGCGCCGGCGGGGCGACATTTATCACAGCGTGTCGCGTG
CCCGACCACGC
```

FIG. 2A

```
ATGTCAATGTCCTACACATGGACAGGCGCCTTGATCACACCATGTGGGCCCGAAGAGGAGAAGTTACCGATCAA
CCCTCTGAGTAATTCGCTCATGCGGTTCCATAATAAGGTGTACTCCACAACCTCAAGGAGTGCCTCTCTGAGGG
CAAAGAAGGTGACTTTTGACAGGGTGCAGGTGCTGGACGCACACTATGACTCAGTCTTGCAGGACGTTAAGCGG
GCCGCCTCTAAGGTTAGTGCGAGGCTCCTCACGGTAGAGGAAGCCTGCGCGCTGACCCCGCCCCACTCCGCCAA
ATCGCGATACGGATTTGGGGCAAAAGAGGTGCGCAGCTTATCCAGGAGGGCCGTTAACCACATCCGGTCCGTGT
GGGAGGACCTCCTGGAAGACCAACATACCCCAATTGACACAACTATCATGGCTAAAAATGAGGTGTTCTGCATT
GATCCAACTAAAGGTGGGAAAAAGCCAGCTCGCCTCATCGTATACCCCGACCTTGGGGTCAGGGTGTGCGAAAA
GATGGCCCTCTATGACATCGCACAAAAGCTTCCCAAAGCGATAATGGGGCCATCCTATGGGTTCCAATACTCTC
CCGCAGAACGGGTCGATTTCCTCCTCAAAGCTTGGGGAAGTAAGAAGGACCCAATGGGGTTCTCGTATGACACC
CGCTGCTTTGACTCAACCGTCACGGAGAGGGACATAAGAACAGAAGAATCCATATATCAGGCTTGTTCTCTGCC
TCAAGAAGCCAGAACTGTCATACACTCGCTCACTGAGAGACTTTACGTAGGAGGGCCCATGACAAACAGCAAAG
GGCAATCCTGCGGCTACAGGCGTTGCCGCGCAAGCGGTGTTTTCACCACCAGCATGGGGAATACCATGACATGT
TACATCAAAGCCCTTGCAGCGTGTAAGGCTGCAGGGATCGTGGACCCTGTTATGTTGGTGTGTGGAGACGACCT
GGTCGTCATCTCAGAGAGCCAAGGTAACGAGGAGGACGAGCGAAACCTGAGAGCTTTCACGGAGGCTATGACCA
GGTATTCCGCCCCTCCCGGTGACCTTCCAGACCGGAATATGACTTGGAGCTTATAACATCCTGCTCCTCAAAC
GTATCGGTAGCGCTGGACTCTCGGGGTCGCCGCCGGTACTTCCTAACCAGAGACCCTACCACTCCAATCACCCG
AGCTGCTTGGGAAACAGTAAGACACTCCCCTGTCAATTCTTGGCTGGGCAACATCATCCAGTACGCCCCACAA
TCTGGGTCCGGATGGTCATAATGACTCACTTCTTCTCCATACTATTGGCCCAGGACACTCTGAACCAAAATCTC
AATTTTGAGATGTACGGGGCAGTATACTCGGTCAATCCATTAGACCTACCGGCCATAATTGAAAGGCTACATGG
GCTTGAAGCCTTTTCACTGCACACATACTCTCCCCACGAACTCTCACGGGTGGCAGCAACTCTCAGAAAACTTG
GAGCGCCTCCCCTTAGAGCGTGGAAGAGTCGGGCGCGTGCCGTGAGCTTCACTCATCGCCCAAGGAGCGAGG
GCGGCCATTTGTGGCCGCTACCTCTTCAACTGGGCGGTGAAAACAAAGCTCAAACTCACTCCATTGCCCGAGGC
GAGCCGCCTGGATTTATCCGGTGGTTCACCGTGGGCGCCGGCGGGGCGACATTTATCACAGCGTGTCGCATG
CCCGACCCCGC
```

FIG. 2B

```
ATGTCAATGTCGTATACATGGACAGGCGCCTTGATCACACCATGTAGTGCTGAGGAGGAGAAACTGCCCATCAG
CCCACTCAGCAATTCTTTGTTGAGACATCATAACCTAGTCTATTCAACGTCGTCGAGAAGCGCTTCCCAGCGTC
AGAGGAAGGTTACCTTCGACAGACTGCAGGTGCTCGACGACCATTATAAGACTGCATTAAAGGAGGTGAAGGAG
CGAGCGTCTAGGGTGAAGGCCCGCATGCTCACCATCGAGGAAGCGTGCGCGCTCGTCCCTCCTCACTCTGCCCG
GTCGAAGTTCGGGTATAGTGCGAAGGACGTTCGCTCCTTGTCCAGCAGGGCCATTGACCAGATCCGCTCCGTCT
GGGAGGACCTGCTGGAAGACACCACAACTCCAATTCCAACCACCATCATGGCGAAGAACGAGGTGTTTTGTGTG
GACCCCGCTAAAGGGGGCCGCAAGCCCGCTCGCCTCATTGTGTACCCTGACCTGGGGGTGCGTGTCTGTGAGAA
ACGCGCCCTATATGACGTGATACAGAAGTTGTCAATTGAGACGATGGGTTCCGCTTATGGATTCCAATACTCGC
CTCAACAGCGGGTCGAACGTCTACTGAAGATGTGGACCTCAAAGAAAACCCCCTTGGGGTTCTCATATGACACC
CGCTGCTTTGACTCAACTGTCACTGAACAGGACATCAGGGTAGAAGAGGAGATATATCAATGCTGTAACCTTGA
ACCGGAGGCCAGGAAAGTGATCTCCTCCCTCACGGAGCGGCTTTACTGCGGGGGCCCTATGTTCAACAGCAAGG
GGGCCCAGTGTGGTTATCGCCGTTGCCGTGCCAGTGGAGTTCTGCCTACCAGCTTTGGCAACACAATCACTTGT
TACATCAAGGCCACAGCGGCCGCGAAGGCCGCAGGCCTCCGGAACCCGGACTTTCTCGTCTGCGGAGATGATTT
GGTCGTGGTGGCTGAAAGTGACGGCGTCGATGAGGATAGAGCAGCCCTGAGAGCCTTCACGGAGGCTATGACCA
GGTACTCTGCTCCACCCGGAGATGCCCCACAGCCCACCTATGACCTTGAGCTCATTACATCTTGCTCCTCTAAC
GTCTCCGTAGCACGGGACGACAAGGGGAGGAGGTATTATTACCTCACCCGTGATGCCACTACTCCCCTAGCCCG
CGCGGCTTGGGAAACAGCCCGTCACACTCCAGTCAACTCCTGGTTAGGTAACATCATCATGTACGCGCCTACTA
TCTGGGTGCGCATGGTAATGATGACACACTTTTTCTCCATACTCCAATCCCAGGAGATACTTGATCGACCCCTT
GACTTTGAAATGTACGGGGCCACTTACTCTGTCACTCCGCTGGATTTACCAGCAATCATTGAAAGACTCCATGG
TCTAAGCGCATTTACGCTCCACAGTTACTCTCCAGTAGAGCTCAATAGGGTCGCGGGGACACTCAGGAAGCTTG
GGTGCCCCCCCTACGAGCTTGGAGACATCGGGCACGAGCAGTGCGCGCCAAGCTTATCGCCCAGGGAGGGAAG
GCCAAAATATGTGGCCTTTATCTCTTCAATTGGGCGGTACGCACCAAGACCAATCTCACTCCACTGCCAGCCAC
TGGCCAGTTGGACTTGTCCAGCTGGTTTACGGTTGGTGTCGGCGGCAACGACATTTATCACAGCGTGTCACGTG
CCCGAACCCGC
```

FIG. 2C

```
ATGTCAATGTCGTATACATGGACAGGCGCCTTGGTAACACCTTGCGCGGCTGAGGAATCAAAGCTGCCAATTAG
CCCCCTGAGCAATTCACTTTTGCGCCATCACAATATGGTGTATGCCACGACCACCCGTTCTGCTGTGACACGGC
AGAAGAAGGTGACCTTCGACCGCCTGCAGGTGGTGGACAGTCACTACAATGAAGTGCTTAAGGAGATAAAGGCA
CGAGCATCCAGAGTGAAGGCACGCTTGCTTACCACAGAGGAAGCTTGCGACCTGACGCCCCCCCACTCAGCCAG
ATCAAAGTTCGGCTACGGGCGAAGGATGTTCGGAGCGCCATTCCCGCAAGGCCATTAACCACATCAGCTCCGTGT
GGAAGGACTTGCTGGACGACAACAATACCCCAATACCAACAACAATCATGGCCAAAAATGAGGTCTTCGCTGTG
AACCCAGCGAAGGGAGGTCGGAAGCCTGCTCGCCTGATCGTGTATCCGGATCTCGGGGTCCGGGTTTGCGAGAA
GAGAGCGCTTCACGACGTCATCAAAAAACTGCCTGAGGCCGTGATGGGAGCCGCTTATGGCTTCCAATACTCCC
CAGCGCAGCGGGTGGAATTTCTTCTGACTGCTTGGAAGTCGAAGAAGACCCCAATGGGGTTCTCTTATGATACC
CGCTGCTTTGACTCCACTGTAACCGAAAAGGACATCAGGGTCGAGGAAGAGGTCTATCAGTGTTGTGACCTGGA
GCCCGAAGCCCGCAAAGTCATCACCGCCCTCACAGATAGACTCTATGTGGGCGGCCCTATGCACAACAGCAAGG
GAGACCTTTGTGGGTATCGGAGATGTCGCGCAAGCGGCGTCTACACCACCAGCTTCGGGAACACGCTGACGTGC
TATCTCAAAGCCACGGCCGCCATCAGGGCGGCGGGGCTGAGAGACTGCACTATGTTGGTTTGCGGTGATGACTT
AGTCGTCATCGCTGAGAGCGACGGCGTAGAGGAGGACAACCGAGCCCTCCGAGCCTTCACGGAGGCTATGACGA
GATACTCGGCTCCCCCAGGTGACGCCCCGCAGCCAGCATATGACCTGGAACTAATAACATCATGTTCATCCAAC
GTCTCAGTCGCGCACGACGTGACGGGTAAAAAGGTATATTACCTAACCCGAGACCCTGAAACTCCCTTGGCGCG
AGCCGCATGGGAGACAGTCCGACACACTCCAGTCAATTCCTGGTTGGGAAACATCATAGTCTACGCTCCCACAA
TATGGGTGCGCATGATATTGATGACCCACTTTTTCTCAATACTCCAGAGCCAGGAAGCCCTTGAGAAAGCACTC
GACTTCGATATGTACGGAGTCACCTACTCTATCACTCCGCTGGATTTACCGGCAATCATTAAAGACTCCATGG
CTTAAGCGCGTTCACGCTGCACGGATACTCTCCACACGAACTCAACCGGGTGGCCGGAGCCCTCAGAAACTTG
GGGTACCCCGCTGAGAGCGTGGAGACATCGGGCCCGAGCAGTCCGCGCTAAGCTTATCGCCCAGGGAGGTAGA
GCCAAAATATGTGGCATATACCTCTTTAACTGGGCGGTAAAAACCAAACTCAAACTCACTCCATTGCCTGCCGC
TGCCAAACTCGATTTATCGGGTTGGTTTACGGTAGGCGCCGGCGGGGAGACATTTATCACAGCATGTCTCATG
CCCGACCCCGC
```

FIG. 2D

```
ATGTCAATGTCGTATACATGGACAGGCGCCTTGATAACACCATGTGCTGCGGAGGAGGAGAAGCTTCCAATAAA
TCCTCTGAGCAACTCCCTCATAAGACACCATAACATGGTGTATTCCACCACATCACGCAGCGCCAGCCTCCGCC
AGAAGAAGGTCACATTTGACAGAGTGCAAGTGTTCGACCAACATTACCAGGAAATACTAAAGGAGATTAAGCTT
CGAGCGTCCAAGGTGCAGGCGAAGCTCTTATCCGTAGAGGAAGCCTGCGACCTCACACCATCGCACTCAGCCCG
GTCCAAATATGGGTATGGTGCACAGGACGTTAGAAGCCATGCTAGCAAGGCCGTCAACCACATCCGCTCCGTGT
GGGAGGACTTGCTAGAAGACTCTGATACTCCAATTCCCACAACCATCATGGCTAAGAATGAAGTCTTCTGCGTA
GATCCGTCGAAGGGTGGACGCAAGCCGGCACGCTTAATAGTTTACCCAGACTTGGGCGTGCGGGTCTGCGAGAA
GATGGCCCTATACGACGTCACGCAGAAGTTACCACAGGCCGTGATGGGTTCAGCATACGGATTCCAGTACTCCC
CCACCCAGAGGGTTGAGTACCTGCTCAAAATGTGGCGGTCAAAGAAGGTGCCTATGGGCTTTTCTTACGACACC
AGGTGTTTTGATTCAACCGTCACTGAGCGGGACATCCGGACTGAGAACGACATCTATCAGTCTTGCCAGCTGGA
TCCCGTAGCAAGGAGGGCAGTATCATCCCTAACGGAACGGCTCTACGTAGGCGGCCCCATGGTGAACTCCAAGG
GACAGTCATGTGGCTACCGTAGATGCCGAGCCAGTGGGGTGCTGCCCACGAGCATGGGAAACACCATCACGTGC
TATCTGAAGGCACAGGCCGCCTGCAGGGCGGCCAACATCAAGGACTGTGACATGTTGGTGTGCGGAGATGACTT
AGTGGTCATTTGTGAGAGTGCTGGCGTCCAGGAGGACACTGAGTCACTGCGAGCATTCACGGATGCTATGACCA
GGTACTCAGCTCCCCCTGGAGACGCCCCGCAACCTACTTACGACCTTGAGCTCATAACATCATGCTCATCCAAT
GTCTCCGTCGCCCACGATGGCAACGGGAAGAGATATTACTACCTCACACGTGACTGTACCACTCCACTTGCGCG
GGCCGCCTGGGAGACAGCCCGCCACACTCCAGTCAACTCGTGGTTGGGCAACATCATTATGTTTGCCCCCACGA
TATGGGTGCGTATGGTTCTGATGACCCATTTTTTCTCCATCCTCCAGTCACAAGAGCAATTGGAGAAAGCACTC
GACTTTGACATCTATGGAGTGACCTATTCCGTCTCTCCACTTGATCTCCCAGCAATCATTCAACGACTCCATGG
CATGGCAGCATTTTCACTCCACGGATACTCTCCAGTTGAGCTCAATAGGGTAGGGCTTGCCTCAGGAAACTTG
GGGTGCCTCCCTTGCGAGCCTGGAGACATCGAGCCAGAGCTGTCAGAGCCAAACTCATTGCCCAAGGGGGGAAA
GCGGCCATATGCGGTAAGTACCTCTTTAACTGGGCAGTGAAGACCAAACTAAAACTCACTCCATTGGTCTCCGC
GAGCAAGCTTGACTTATCAGGCTGGTTCGTGGCCGGCTACGACGGGGGGGACATTTATCACAGCGTGTCCCAGG
CTCGACCCCGT
```

FIG. 2E

SEQUENCE LISTING

<160> NUMBER OF SEQ ID NOS: 28

<210> SEQ ID NO 1
<211> LENGTH: 571
<212> TYPE: PRT
<213> ORGANISM: Artificial Sequence
<220> FEATURE:
<223> OTHER INFORMATION: modified HCV NS5B

<400> SEQUENCE: 1

Met Ser Met Ser Tyr Thr Trp Thr Gly Ala Leu Ile Thr Pro Cys Ser
1               5                   10                  15

Pro Glu Glu Glu Lys Leu Pro Ile Asn Pro Leu Ser Asn Ser Leu Leu
            20                  25                  30

Arg Tyr His Asn Lys Val Tyr Cys Thr Thr Lys Ser Ala Ser Leu
        35                  40                  45

-continued

```
Arg Ala Lys Lys Val Thr Phe Asp Arg Met Gln Val Leu Asp Ser Tyr
 50                  55                  60
Tyr Asp Ser Val Leu Lys Asp Ile Lys Leu Ala Ala Ser Lys Val Thr
 65                  70                  75                  80
Ala Arg Leu Leu Thr Met Glu Glu Ala Cys Gln Leu Thr Pro Pro His
                 85                  90                  95
Ser Ala Arg Ser Lys Tyr Gly Phe Gly Ala Lys Glu Val Arg Ser Leu
                100                 105                 110
Ser Gly Arg Ala Val Asn His Ile Lys Ser Val Trp Lys Asp Leu Leu
                115                 120                 125
Glu Asp Ser Glu Thr Pro Ile Pro Thr Thr Ile Met Ala Lys Asn Glu
130                 135                 140
Val Phe Cys Val Asp Pro Thr Lys Gly Lys Lys Ala Ala Arg Leu
145                 150                 155                 160
Ile Val Tyr Pro Asp Leu Gly Val Arg Val Cys Glu Lys Met Ala Leu
                165                 170                 175
Tyr Asp Ile Thr Gln Lys Leu Pro Gln Ala Val Met Gly Ala Ser Tyr
                180                 185                 190
Gly Phe Gln Tyr Ser Pro Ala Gln Arg Val Glu Phe Leu Leu Lys Ala
                195                 200                 205
Trp Ala Glu Lys Lys Asp Pro Met Gly Phe Ser Tyr Asp Thr Arg Cys
210                 215                 220
Phe Asp Ser Thr Val Thr Glu Arg Asp Ile Arg Thr Glu Glu Ser Ile
225                 230                 235                 240
Tyr Arg Ala Cys Ser Leu Pro Glu Glu Ala His Thr Ala Ile His Ser
                245                 250                 255
Leu Thr Glu Arg Leu Tyr Val Gly Gly Pro Met Phe Asn Ser Lys Gly
                260                 265                 270
Gln Thr Cys Gly Tyr Arg Arg Cys Arg Ala Ser Gly Val Leu Thr Thr
                275                 280                 285
Ser Met Gly Asn Thr Ile Thr Cys Tyr Val Lys Ala Leu Ala Ala Cys
290                 295                 300
Lys Ala Ala Gly Ile Ile Ala Pro Thr Met Leu Val Cys Gly Asp Asp
305                 310                 315                 320
Leu Val Val Ile Ser Glu Ser Gln Gly Thr Glu Glu Asp Glu Arg Asn
                325                 330                 335
Leu Arg Ala Phe Thr Glu Ala Met Thr Arg Tyr Ser Ala Pro Pro Gly
                340                 345                 350
Asp Pro Pro Arg Pro Glu Tyr Asp Leu Glu Leu Ile Thr Ser Cys Ser
                355                 360                 365
Ser Asn Val Ser Val Ala Leu Gly Pro Gln Gly Arg Arg Tyr Tyr
                370                 375                 380
Leu Thr Arg Asp Pro Thr Thr Pro Ile Ala Arg Ala Ala Trp Glu Thr
385                 390                 395                 400
Val Arg His Ser Pro Val Asn Ser Trp Leu Gly Asn Ile Ile Gln Tyr
                405                 410                 415
Ala Pro Thr Ile Trp Ala Arg Met Val Leu Met Thr His Phe Phe Ser
                420                 425                 430
Ile Leu Met Ala Gln Asp Thr Leu Asp Gln Asn Leu Asn Phe Glu Met
                435                 440                 445
Tyr Gly Ala Val Tyr Ser Val Ser Pro Leu Asp Leu Pro Ala Ile Ile
450                 455                 460
```

```
Glu Arg Leu His Gly Leu Asp Ala Phe Ser Leu His Thr Tyr Thr Pro
465                 470                 475                 480

His Glu Leu Thr Arg Val Ala Ser Ala Leu Arg Lys Leu Gly Ala Pro
                485                 490                 495

Pro Leu Arg Ala Trp Lys Ser Arg Ala Arg Ala Val Arg Ala Ser Leu
            500                 505                 510

Ile Ser Arg Gly Gly Arg Ala Ala Val Cys Gly Arg Tyr Leu Phe Asn
        515                 520                 525

Trp Ala Val Lys Thr Lys Leu Lys Leu Thr Pro Leu Pro Glu Ala Arg
    530                 535                 540

Leu Leu Asp Leu Ser Ser Trp Phe Thr Val Gly Ala Gly Gly Gly Asp
545                 550                 555                 560

Ile Tyr His Ser Val Ser Arg Ala Arg Pro Arg
                565                 570
```

<210> SEQ ID NO 2
<211> LENGTH: 571
<212> TYPE: PRT
<213> ORGANISM: Artificial Sequence
<220> FEATURE:
<223> OTHER INFORMATION: modified HCV NS5B

<400> SEQUENCE: 2

```
Met Ser Met Ser Tyr Thr Trp Thr Gly Ala Leu Ile Thr Pro Cys Gly
1               5                   10                  15

Pro Glu Glu Lys Leu Pro Ile Asn Pro Leu Ser Asn Ser Leu Met
            20                  25                  30

Arg

```
Leu Thr Glu Arg Leu Tyr Val Gly Gly Pro Met Thr Asn Ser Lys Gly
        260                 265                 270

Gln Ser Cys Gly Tyr Arg Arg Cys Arg Ala Ser Gly Val Phe Thr Thr
        275                 280                 285

Ser Met Gly Asn Thr Met Thr Cys Tyr Ile Lys Ala Leu Ala Ala Cys
        290                 295                 300

Lys Ala Ala Gly Ile Val Asp Pro Val Met Leu Val Cys Gly Asp Asp
305                 310                 315                 320

Leu Val Val Ile Ser Glu Ser Gln Gly Asn Glu Glu Asp Glu Arg Asn
                325                 330                 335

Leu Arg Ala Phe Thr Glu Ala Met Thr Arg Tyr Ser Ala Pro Pro Gly
                340                 345                 350

Asp Leu Pro Arg Pro Glu Tyr Asp Leu Glu Leu Ile Thr Ser Cys Ser
                355                 360                 365

Ser Asn Val Ser Val Ala Leu Asp Ser Arg Gly Arg Arg Arg Tyr Phe
        370                 375                 380

Leu Thr Arg Asp Pro Thr Thr Pro Ile Thr Arg Ala Ala Trp Glu Thr
385                 390                 395                 400

Val Arg His Ser Pro Val Asn Ser Trp Leu Gly Asn Ile Ile Gln Tyr
                405                 410                 415

Ala Pro Thr Ile Trp Val Arg Met Val Ile Met Thr His Phe Phe Ser
                420                 425                 430

Ile Leu Leu Ala Gln Asp Thr Leu Asn Gln Asn Leu Asn Phe Glu Met
                435                 440                 445

Tyr Gly Ala Val Tyr Ser Val Asn Pro Leu Asp Leu Pro Ala Ile Ile
                450                 455                 460

Glu Arg Leu His Gly Leu Glu Ala Phe Ser Leu His Thr Tyr Ser Pro
465                 470                 475                 480

His Glu Leu Ser Arg Val Ala Ala Thr Leu Arg Lys Leu Gly Ala Pro
                485                 490                 495

Pro Leu Arg Ala Trp Lys Ser Arg Ala Arg Ala Val Arg Ala Ser Leu
                500                 505                 510

Ile Ala Gln Gly Ala Arg Ala Ala Ile Cys Gly Arg Tyr Leu Phe Asn
                515                 520                 525

Trp Ala Val Lys Thr Lys Leu Lys Leu Thr Pro Leu Pro Glu Ala Ser
530                 535                 540

Arg Leu Asp Leu Ser Gly Trp Phe Thr Val Gly Ala Gly Gly Gly Asp
545                 550                 555                 560

Ile Tyr His Ser Val Ser His Ala Arg Pro Arg
                565                 570

<210> SEQ ID NO 3
<211> LENGTH: 571
<212> TYPE: PRT
<213> ORGANISM: Artificial Sequence
<220> FEATURE:
<223> OTHER INFORMATION: modified HCV NS5B

<400> SEQUENCE: 3

Met Ser Met Ser Tyr Thr Trp Thr Gly Ala Leu Ile Thr Pro Cys Ser
  1               5                  10                  15

Ala Glu Glu Glu Lys Leu Pro Ile Ser Pro Leu Ser Asn Ser Leu Leu
                 20                  25                  30

Arg His His Asn Leu Val Tyr Ser Thr Ser Ser Arg Ser Ala Ser Gln
            35                  40                  45
```

-continued

```
Arg Gln Arg Lys Val Thr Phe Asp Arg Leu Gln Val Leu Asp Asp His
     50                  55                  60

Tyr Lys Thr Ala Leu Lys Glu Val Lys Glu Arg Ala Ser Arg Val Lys
 65                  70                  75                  80

Ala Arg Met Leu Thr Ile Glu Glu Ala Cys Ala Leu Val Pro Pro His
                     85                  90                  95

Ser Ala Arg Ser Lys Phe Gly Tyr Ser Ala Lys Asp Val Arg Ser Leu
                100                 105                 110

Ser Ser Arg Ala Ile Asp Gln Ile Arg Ser Val Trp Glu Asp Leu Leu
            115                 120                 125

Glu Asp Thr Thr Pro Ile Pro Thr Thr Ile Met Ala Lys Asn Glu
    130                 135                 140

Val Phe Cys Val Asp Pro Ala Lys Gly Gly Arg Lys Pro Ala Arg Leu
145                 150                 155                 160

Ile Val Tyr Pro Asp Leu Gly Val Arg Val Cys Glu Lys Arg Ala Leu
                165                 170                 175

Tyr Asp Val Ile Gln Lys Leu Ser Ile Glu Thr Met Gly Ser Ala Tyr
                180                 185                 190

Gly Phe Gln Tyr Ser Pro Gln Gln Arg Val Glu Arg Leu Leu Lys Met
            195                 200                 205

Trp Thr Ser Lys Lys Thr Pro Leu Gly Phe Ser Tyr Asp Thr Arg Cys
    210                 215                 220

Phe Asp Ser Thr Val Thr Glu Gln Asp Ile Arg Val Glu Glu Glu Ile
225                 230                 235                 240

Tyr Gln Cys Cys Asn Leu Glu Pro Glu Ala Arg Lys Val Ile Ser Ser
                245                 250                 255

Leu Thr Glu Arg Leu Tyr Cys Gly Gly Pro Met Phe Asn Ser Lys Gly
            260                 265                 270

Ala Gln Cys Gly Tyr Arg Arg Cys Arg Ala Ser Gly Val Leu Pro Thr
    275                 280                 285

Ser Phe Gly Asn Thr Ile Thr Cys Tyr Ile Lys Ala Thr Ala Ala Ala
    290                 295                 300

Lys Ala Ala Gly Leu Arg Asn Pro Asp Phe Leu Val Cys Gly Asp Asp
305                 310                 315                 320

Leu Val Val Val Ala Glu Ser Asp Gly Val Asp Glu Asp Arg Ala Ala
                325                 330                 335

Leu Arg Ala Phe Thr Glu Ala Met Thr Arg Tyr Ser Ala Pro Pro Gly
                340                 345                 350

Asp Ala Pro Gln Pro Thr Tyr Asp Leu Glu Leu Ile Thr Ser Cys Ser
            355                 360                 365

Ser Asn Val Ser Val Ala Arg Asp Asp Lys Gly Arg Arg Tyr Tyr Tyr
    370                 375                 380

Leu Thr Arg Asp Ala Thr Thr Pro Leu Ala Arg Ala Ala Trp Glu Thr
385                 390                 395                 400

Ala Arg His Thr Pro Val Asn Ser Trp Leu Gly Asn Ile Ile Met Tyr
                405                 410                 415

Ala Pro Thr Ile Trp Val Arg Met Val Met Met Thr His Phe Phe Ser
                420                 425                 430

Ile Leu Gln Ser Gln Glu Ile Leu Asp Arg Pro Leu Asp Phe Glu Met
            435                 440                 445

Tyr Gly Ala Thr Tyr Ser Val Thr Pro Leu Asp Leu Pro Ala Ile Ile
450                 455                 460
```

-continued

```
Glu Arg Leu His Gly Leu Ser Ala Phe Thr Leu His Ser Tyr Ser Pro
465                 470                 475                 480

Val Glu Leu Asn Arg Val Ala Gly Thr Leu Arg Lys Leu Gly Cys Pro
                485                 490                 495

Pro Leu Arg Ala Trp Arg His Arg Ala Arg Ala Val Arg Ala Lys Leu
            500                 505                 510

Ile Ala Gln Gly Gly Lys Ala Lys Ile Cys Gly Leu Tyr Leu Phe Asn
        515                 520                 525

Trp Ala Val Arg Thr Lys Thr Asn Leu Thr Pro Leu Pro Ala Thr Gly
    530                 535                 540

Gln Leu Asp Leu Ser Ser Trp Phe Thr Val Gly Val Gly Gly Asn Asp
545                 550                 555                 560

Ile Tyr His Ser Val Ser Arg Ala Arg Thr Arg
                565                 570

<210> SEQ ID NO 4
<211> LENGTH: 571
<212> TYPE: PRT
<213> ORGANISM: Artificial Sequence
<220> FEATURE:
<223> OTHER INFORMATION: modified HCV NS5B

<400> SEQUENCE: 4

Met Ser Met Ser Tyr Thr Trp Thr Gly Ala Leu Val Thr Pro Cys Ala
1               5                   10                  15

Ala Glu Glu Ser Lys Leu Pro Ile Ser Pro Leu Ser Asn Ser Leu Leu
            20

-continued

Leu Thr Asp Arg Leu Tyr Val Gly Gly Pro Met His Asn Ser Lys Gly
            260                 265                 270

Asp Leu Cys Gly Tyr Arg Arg Cys Arg Ala Ser Gly Val Tyr Thr Thr
        275                 280                 285

Ser Phe Gly Asn Thr Leu Thr Cys Tyr Leu Lys Ala Thr Ala Ala Ile
    290                 295                 300

Arg Ala Ala Gly Leu Arg Asp Cys Thr Met Leu Val Cys Gly Asp Asp
305                 310                 315                 320

Leu Val Val Ile Ala Glu Ser Asp Gly Val Glu Asp Asn Arg Ala
                325                 330                 335

Leu Arg Ala Phe Thr Glu Ala Met Thr Arg Tyr Ser Ala Pro Pro Gly
            340                 345                 350

Asp Ala Pro Gln Pro Ala Tyr Asp Leu Glu Leu Ile Thr Ser Cys Ser
        355                 360                 365

Ser Asn Val Ser Val Ala His Asp Val Thr Gly Lys Lys Val Tyr Tyr
    370                 375                 380

Leu Thr Arg Asp Pro Glu Thr Pro Leu Ala Arg Ala Ala Trp Glu Thr
385                 390                 395                 400

Val Arg His Thr Pro Val Asn Ser Trp Leu Gly Asn Ile Ile Val Tyr
                405                 410                 415

Ala Pro Thr Ile Trp Val Arg Met Ile Leu Met Thr His Phe Phe Ser
            420                 425                 430

Ile Leu Gln Ser Gln Glu Ala Leu Glu Lys Ala Leu Asp Phe Asp Met
        435                 440                 445

Tyr Gly Val Thr Tyr Ser Ile Thr Pro Leu Asp Leu Pro Ala Ile Ile
    450                 455                 460

Gln Arg Leu His Gly Leu Ser Ala Phe Thr Leu His Gly Tyr Ser Pro
465                 470                 475                 480

His Glu Leu Asn Arg Val Ala Gly Ala Leu Arg Lys Leu Gly Val Pro
                485                 490                 495

Pro Leu Arg Ala Trp Arg His Arg Ala Arg Ala Val Arg Ala Lys Leu
            500                 505                 510

Ile Ala Gln Gly Gly Arg Ala Lys Ile Cys Gly Ile Tyr Leu Phe Asn
        515                 520                 525

Trp Ala Val Lys Thr Lys Leu Lys Leu Thr Pro Leu Pro Ala Ala Ala
    530                 535                 540

Lys Leu Asp Leu Ser Gly Trp Phe Thr Val Gly Ala Gly Gly Gly Asp
545                 550                 555                 560

Ile Tyr His Ser Met Ser His Ala Arg Pro Arg
                565                 570

<210> SEQ ID NO 5
<211> LENGTH: 571
<212> TYPE: PRT
<213> ORGANISM: Artificial Sequence
<220> FEATURE:
<223> OTHER INFORMATION: modified HCV NS5B

<400> SEQUENCE: 5

Met Ser Met Ser Tyr Thr Trp Thr Gly Ala Leu Ile Thr Pro Cys Ala
 1               5                  10                  15

Ala Glu Glu Glu Lys Leu Pro Ile Asn Pro Leu Ser Asn Ser Leu Ile
                20                  25                  30

Arg His His Asn Met Val Tyr Ser Thr Thr Ser Arg Ser Ala Ser Leu
            35                  40                  45

-continued

```
Arg Gln Lys Lys Val Thr Phe Asp Arg Val Gln Val Phe Asp Gln His
 50                  55                  60

Tyr Gln Glu Ile Leu Lys Glu Ile Lys Leu Arg Ala Ser Lys Val Gln
 65                  70                  75                  80

Ala Lys Leu Leu Ser Val Glu Glu Ala Cys Asp Leu Thr Pro Ser His
                 85                  90                  95

Ser Ala Arg Ser Lys Tyr Gly Tyr Gly Ala Gln Asp Val Arg Ser His
                100                 105                 110

Ala Ser Lys Ala Val Asn His Ile Arg Ser Val Trp Glu Asp Leu Leu
            115                 120                 125

Glu Asp Ser Asp Thr Pro Ile Pro Thr Thr Ile Met Ala Lys Asn Glu
130                 135                 140

Val Phe Cys Val Asp Pro Ser Lys Gly Arg Lys Pro Ala Arg Leu
145                 150                 155                 160

Ile Val Tyr Pro Asp Leu Gly Val Arg Val Cys Glu Lys Met Ala Leu
                165                 170                 175

Tyr Asp Val Thr Gln Lys Leu Pro Gln Ala Val Met Gly Ser Ala Tyr
                180                 185                 190

Gly Phe Gln Tyr Ser Pro Thr Gln Arg Val Glu Tyr Leu Leu Lys Met
            195                 200                 205

Trp Arg Ser Lys Lys Val Pro Met Gly Phe Ser Tyr Asp Thr Arg Cys
210                 215                 220

Phe Asp Ser Thr Val Thr Glu Arg Asp Ile Arg Thr Glu Asn Asp Ile
225                 230                 235                 240

Tyr Gln Ser Cys Gln Leu Asp Pro Val Ala Arg Ala Val Ser Ser
                245                 250                 255

Leu Thr Glu Arg Leu Tyr Val Gly Gly Pro Met Val Asn Ser Lys Gly
            260                 265                 270

Gln Ser Cys Gly Tyr Arg Arg Cys Arg Ala Ser Gly Val Leu Pro Thr
        275                 280                 285

Ser Met Gly Asn Thr Ile Thr Cys Tyr Leu Lys Ala Gln Ala Ala Cys
290                 295                 300

Arg Ala Ala Asn Ile Lys Asp Cys Asp Met Leu Val Cys Gly Asp Asp
305                 310                 315                 320

Leu Val Val Ile Cys Glu Ser Ala Gly Val Gln Glu Asp Thr Glu Ser
                325                 330                 335

Leu Arg Ala Phe Thr Asp Ala Met Thr Arg Tyr Ser Ala Pro Pro Gly
            340                 345                 350

Asp Ala Pro Gln Pro Thr Tyr Asp Leu Glu Leu Ile Thr Ser Cys Ser
        355                 360                 365

Ser Asn Val Ser Val Ala His Asp Gly Asn Gly Lys Arg Tyr Tyr Tyr
    370                 375                 380

Leu Thr Arg Asp Cys Thr Thr Pro Leu Ala Arg Ala Ala Trp Glu Thr
385                 390                 395                 400

Ala Arg His Thr Pro Val Asn Ser Trp Leu Gly Asn Ile Ile Met Phe
                405                 410                 415

Ala Pro Thr Ile Trp Val Arg Met Val Leu Met Thr His Phe Phe Ser
            420                 425                 430

Ile Leu Gln Ser Gln Glu Gln Leu Glu Lys Ala Leu Asp Phe Asp Ile
        435                 440                 445

Tyr Gly Val Thr Tyr Ser Val Ser Pro Leu Asp Leu Pro Ala Ile Ile
    450                 455                 460
```

```
Gln Arg Leu His Gly Met Ala Ala Phe Ser Leu His Gly Tyr Ser Pro
465                 470                 475                 480

Val Glu Leu Asn Arg Val Gly Ala Cys Leu Arg Lys Leu Gly Val Pro
            485                 490                 495

Pro Leu Arg Ala Trp Arg His Arg Ala Arg Ala Val Arg Ala Lys Leu
        500                 505                 510

Ile Ala Gln Gly Gly Lys Ala Ala Ile Cys Gly Lys Tyr Leu Phe Asn
    515                 520                 525

Trp Ala Val Lys Thr Lys Leu Lys Leu Thr Pro Leu Val Ser Ala Ser
530                 535                 540

Lys Leu Asp Leu Ser Gly Trp Phe Val Ala Gly Tyr Asp Gly Gly Asp
545                 550                 555                 560

Ile Tyr His Ser Val Ser Gln Ala Arg Pro Arg
                565                 570
```

<210> SEQ ID NO 6
<211> LENGTH: 1713
<212> TYPE: DNA
<213> ORGANISM: Artificial Sequence
<220> FEATURE:
<223> OTHER INFORMATION: nucleotide sequence encoding SEQ ID NO: 1

<400> SEQUENCE: 6

| | | |
|---|---|---|
| atgtcaatgt cgtatacatg gacaggcgcc ttgatcactc cttgtagtcc cgaagaggag | 60 |
| aagttaccga ttaacccctt gagcaactcc ctgttgcgat atcacaacaa ggtgtactgt | 120 |
| accacaacaa agagcgcctc actaagggct aaaaaggtaa cttttgatag gatgcaagtg | 180 |
| ctcgactcct actacgactc agtcttaaag gacattaagc tagcggcctc caaggtcacc | 240 |
| gcaaggctcc tcaccatgga ggaggcttgc agttaaccc cacccccattc tgcaagatct | 300 |
| aaatatgggt ttggggctaa ggaggtccgc agcttgtccg ggagggccgt taaccacatc | 360 |
| aagtccgtgt ggaaggacct cctggaggac tcagaaacac caattcccac aaccattatg | 420 |
| gccaaaaatg aggtgttctg cgtggacccc accaaggggg caagaaagc agctcgcctt | 480 |
| atcgtttacc ctgacctcgg cgtcaggtc tgcgagaaga tggccccttta tgacattaca | 540 |
| caaaaacttc tcaggcggt gatgggggct tcttatggat tccagtattc ccccgctcag | 600 |
| cgggtagagt ttctcttgaa agcatgggcg aaaagaagg acccctatggg tttttcgtat | 660 |
| gatacccgat gctttgactc aaccgtcact gagagagaca tcaggactga ggagtccata | 720 |
| tatcgggcct gctccttgcc cgaggaggcc cacactgcca tacactcgct aactgagaga | 780 |
| cttttacgtgg gagggcctat gttcaacagc aagggccaaa cctgcgggta caggcgttgc | 840 |
| cgcgccagcg gggtgctcac cactagcatg gggaacacca tcacatgcta cgtgaaagcc | 900 |
| ttagcggctt gtaaagctgc agggataatc gcgcccacaa tgctggtatg cggcgatgac | 960 |
| ttggttgtca tctcagaaag ccaggggacc gaggaggacg agcggaacct gagagccttc | 1020 |
| acggaggcta tgaccaggta ttctgcccct cctggtgacc cccccagacc ggagtatgat | 1080 |
| ctggagctga taacatcttg ctcctcaaat gtgtctgtgg cgctgggccc acaaggccgc | 1140 |
| cgcagatact acctgaccag agaccctacc actccaatcg cccgggctgc ctgggaaaca | 1200 |
| gttagacact cccctgtcaa ttcatggctg ggaaacatca tccagtacgc cccgaccata | 1260 |
| tgggctcgca tggtcctgat gacacacttc ttctccattc tcatggctca agacacgctg | 1320 |
| gaccagaacc tcaactttga gatgtacgga gcggtgtact ccgtgagtcc cttggacctc | 1380 |
| ccagctataa ttgaaaggtt acatgggctt gacgcttttt ctctgcacac atacactccc | 1440 |

```
cacgaactga cacgggtggc ttcagccctc agaaaacttg gggcgccacc cctcagagcg      1500
tggaagagcc gggcacgtgc agtcagggcg tccctcatct cccgtggggg gagagcggcc      1560
gtctgcggtc gatatctctt caactgggcg gtgaagacca agctcaaact cactccattg      1620
ccggaggcgc gcctcctgga tttatccagc tggttcaccg tcggcgccgg cggggcgac       1680 atttatcaca gcgtgtcgcg tgcccgacca cgc                                   1713
```

<210> SEQ ID NO 7
<211> LENGTH: 1713
<212> TYPE: DNA
<213> ORGANISM: Artificial Sequence
<220> FEATURE:
<223> OTHER INFORMATION: nucleotide sequence encoding SEQ ID NO: 2

<400> SEQUENCE: 7

```
atgtcaatgt cctacacatg gacaggcgcc ttgatcacac catgtgggcc cgaagaggag        60
aagttaccga tcaaccctct gagtaattcg ctcatgcggt tccataataa ggtgtactcc       120
acaacctcaa ggagtgcctc tctgagggca agaaggtgac ttttgacag ggtgcaggtg       180 ctggacgcac actatgactc agtcttgcag gacgttaagc gggccgcctc taaggttagt       240
gcgaggctcc tcacggtaga ggaagcctgc gcgctgaccc cgccccactc cgccaaatcg       300
cgatacggat ttggggcaaa agaggtgcgc agcttatcca ggagggccgt taaccacatc       360
cggtccgtgt gggaggacct cctggaagac caacataccc caattgacac aactatcatg       420
gctaaaaatg aggtgttctg cattgatcca actaaaggtg ggaaaaagcc agctcgcctc       480
atcgtatacc ccgaccttgg ggtcaggggtg tgcgaaaaga tggccctcta tgacatcgca       540
caaaagcttc ccaaagcgat aatggggcca tcctatgggt tccaatactc tcccgcagaa       600
cgggtcgatt tcctcctcaa agcttgggga agtaagaagg acccaatggg gttctcgtat       660
gacacccgct gctttgactc aaccgtcacg gagagggaca taagaacaga gaatccata        720 tatcaggctt gttctctgcc tcaagaagcc agaactgtca tacactcgct cactgagaga       780
ctttacgtag agggcccat gacaaacagc aaagggcaat cctgcggcta caggcgttgc       840
cgcgcaagcg tgttttcac caccagcatg gggaatacca tgacatgtta catcaaagcc       900
cttgcagcgt gtaaggctgc agggatcgtg accctgttat tgttggtgtg tggagacgac       960
ctggtcgtca tctcagagag ccaaggtaac gaggaggacg agcgaaacct gagagctttc      1020
acggaggcta tgaccaggta ttccgcccct cccggtgacc ttcccagacc ggaatatgac      1080
ttggagctta acatcctg ctcctcaaac gtatcggtag cgctggactc tcggggtcgc      1140
cgccggtact tcctaaccag agaccctacc actccaatca cccgagctgc ttgggaaaca      1200
gtaagacact cccctgtcaa ttcttggctg ggcaacatca tccagtacgc ccccacaatc      1260
tgggtccgga tggtcataat gactcacttc ttctccatac tattggccca ggacactctg      1320
aaccaaaatc tcaattttga gatgtacggg gcagtatact cggtcaatcc attagaccta      1380
ccggccataa ttgaaaggct acatgggctt gaagcctttt cactgcacac atactctccc      1440
cacgaactct cacgggtggc agcaactctc agaaaacttg gagcgcctcc ccttagagcg      1500
tggaagagtc gggcgcgtgc cgtgagagct tcactcatcg cccaaggagc gagggcggcc      1560
atttgtggcc gctacctctt caactgggcg gtgaaaacaa agctcaaact cactccattg      1620
cccgaggcga gccgcctgga tttatccggg tggttcaccg tgggcgccgg cggggcgac       1680 atttatcaca gcgtgtcgca tgcccgaccc cgc                                   1713
```

<210> SEQ ID NO 8
<211> LENGTH: 1713
<212> TYPE: DNA
<213> ORGANISM: Artificial Sequence
<220> FEATURE:
<223> OTHER INFORMATION: nucleotide sequence encoding SEQ ID NO: 3

<400> SEQUENCE: 8

```
atgtcaatgt cgtatacatg gacaggcgcc ttgatcacac catgtagtgc tgaggaggag      60
aaactgccca tcagcccact cagcaattct ttgttgagac atcataacct agtctattca     120
acgtcgtcga gaagcgcttc ccagcgtcag aggaaggtta ccttcgacag actgcaggtg     180
ctcgacgacc attataagac tgcattaaag gaggtgaagg agcgagcgtc tagggtgaag     240
gcccgcatgc tcaccatcga ggaagcgtgc gcgctcgtcc ctcctcactc tgcccggtcg     300
aagttcgggt atagtgcgaa ggacgttcgc tccttgtcca gcagggccat tgaccagatc     360
cgctccgtct gggaggacct gctggaagac accacaactc caattccaac caccatcatg     420
gcgaagaacg aggtgttttg tgtggacccc gctaaagggg gccgcaagcc cgctcgcctc     480
attgtgtacc ctgacctggg ggtgcgtgtc tgtgagaaac gcgccctata tgacgtgata     540
cagaagttgt caattgagac gatgggttcc gcttatggat tccaatactc gcctcaacag     600
cgggtcgaac gtctactgaa gatgtggacc tcaaagaaaa ccccccttggg gttctcatat     660
gacacccgct gctttgactc aactgtcact gaacaggaca tcagggtaga agaggagata     720
tatcaatgct gtaaccttga accggaggcc aggaaagtga tctcctcccct cacgagcgg     780
cttactgcg ggggccctat gttcaacagc aaggggccc agtgtggtta tcgccgttgc     840
cgtgccagtg gagttctgcc taccagcttt ggcaacacaa tcacttgtta catcaaggcc     900
acagcggccg cgaaggccgc aggcctccgg aacccggact ttctcgtctg cggagatgat    960
ttggtcgtgg tggctgaaag tgacggcgtc gatgaggata gagcagccct gagagccttc    1020
acggaggcta tgaccaggta ctctgctcca cccggagatg ccccacagcc cacctatgac    1080
cttgagctca ttacatcttg ctcctctaac gtctccgtag cacgggacga caaggggagg    1140
aggtattatt acctcacccg tgatgccact actcccctag cccgcgcggc ttgggaaaca    1200
gcccgtcaca ctccagtcaa ctcctggtta ggtaacatca tcatgtacgc gcctactatc    1260
tgggtgcgca tggtaatgat gacacacttt ttctccatac tccaatccca ggagatactt    1320
gatcgacccc ttgactttga aatgtacggg gccacttact ctgtcactcc gctggattta    1380
ccagcaatca ttgaaagact ccatggtcta agcgcattta cgctccacag ttactctcca    1440
gtagagctca atagggtcgc ggggacactc aggaagcttg ggtgcccccc cctacgagct    1500
tggagacatc gggcacgagc agtgcgcgcc aagcttatcg cccagggagg gaaggccaaa    1560
atatgtggcc tttatctctt caattgggcg gtacgcacca agaccaatct cactccactg    1620
ccagccactg gccagttgga cttgtccagc tggtttacgg ttggtgtcgg cgggaacgac    1680
atttatcaca gcgtgtcacg tgcccgaacc cgc                                 1713
```

<210> SEQ ID NO 9
<211> LENGTH: 1713
<212> TYPE: DNA
<213> ORGANISM: Artificial Sequence
<220> FEATURE:
<223> OTHER INFORMATION: nucleotide sequence encoding SEQ ID NO: 4

<400> SEQUENCE: 9

```
atgtcaatgt cgtatacatg acaggcgcc ttggtaacac cttgcgcggc tgaggaatca      60
aagctgccaa ttagccccct gagcaattca cttttgcgcc atcacaatat ggtgtatgcc    120
acgaccaccc gttctgctgt gacacggcag aagaaggtga ccttcgaccg cctgcaggtg    180
gtggacagtc actacaatga agtgcttaag gagataaagg cacgagcatc cagagtgaag    240
gcacgcttgc ttaccacaga ggaagcttgc gacctgacgc cccccactc agccagatca     300
aagttcggct acggggcgaa ggatgttcgg agccattccc gcaaggccat taaccacatc    360
agctccgtgt ggaaggactt gctggacgac aacaataccc caataccaac acaatcatg    420
gccaaaaatg aggtcttcgc tgtgaaccca gcgaagggag gtcggaagcc tgctcgcctg    480
atcgtgtatc cggatctcgg ggtccgggtt tgcgagaaga gagcgcttca cgacgtcatc    540
aaaaaactgc ctgaggccgt gatgggagcc gcttatggct ccaatactc cccagcgcag     600
cgggtggaat tcttctgac tgcttggaag tcgaagaaga ccccaatggg gttctcttat     660
gatacccgct gctttgactc cactgtaacc gaaaaggaca tcagggtcga ggaagaggtc    720
tatcagtgtt gtgacctgga gcccgaagcc cgcaaagtca tcaccgccct cacagataga    780
ctctatgtgg gcggccctat gcacaacagc aagggagacc tttgtgggta tcggagatgt    840
cgcgcaagcg cgtctacac caccagcttc gggaacacgc tgacgtgcta tctcaaagcc    900
acggccgcca tcagggcggc ggggctgaga gactgcacta tgttggtttg cggtgatgac    960
ttagtcgtca tcgctgagag cgacggcgta gaggaggaca accgagccct ccgagccttc   1020
acggaggcta tgacgagata tcggctcccc caggtgacg ccccgcagcc agcatatgac    1080
ctgaactaa taacatcatg ttcatccaac gtctcagtcg cgcacgacgt gacgggtaaa    1140
aaggtatatt acctaacccg agaccctgaa actccctgg cgcgagccgc atgggagaca    1200
gtccgacaca ctccagtcaa ttcctggttg ggaaacatca tagtctacgc tcccacaata   1260
tgggtgcgca tgatattgat gacccacttt ttctcaatac tccagagcca ggaagcccctt  1320
gagaaagcac tcgacttcga tatgtacgga gtcacctact ctatcactcc gctggattta   1380
ccggcaatca ttcaaagact ccatggctta agcgcgttca cgctgcacgg atactctcca   1440
cacgaactca accgggtggc cggagccctc agaaaacttg ggtaccccc gctgagagcg    1500
tggagacatc gggcccgagc agtccgcgct aagcttatcg cccagggagg tagagccaaa   1560
atatgtggca tacctctt taactgggcg gtaaaaacca aactcaaact cactccattg     1620
cctgccgctg ccaaactcga tttatcgggt tggtttacgg taggcgccgg cggggagac    1680
atttatcaca gcatgtctca tgcccgaccc cgc                                1713
```

<210> SEQ ID NO 10
<211> LENGTH: 1713
<212> TYPE: DNA
<213> ORGANISM: Artificial Sequence
<220> FEATURE:
<223> OTHER INFORMATION: nucleotide sequence encoding SEQ ID NO: 5

<400> SEQUENCE: 10

```
atgtcaatgt cgtatacatg acaggcgcc ttgataacac catgtgctgc ggaggaggag      60
aagcttccaa taaatcctct gagcaactcc ctcataagac accataacat ggtgtattcc    120
accacatcac gcagcgccag cctccgccag aagaaggtca catttgacag agtgcaagtg    180
ttcgaccaac attaccagga aatactaaag gagattaagg ttcgagcgtc caaggtgcag    240
gcgaagctct tatccgtaga ggaagcctgc gacctcacac catcgcactc agcccggtcc    300
```

-continued

```
aaatatgggt atggtgcaca ggacgttaga agccatgcta gcaaggccgt caaccacatc    360
cgctccgtgt gggaggactt gctagaagac tctgatactc caattcccac aaccatcatg    420
gctaagaatg aagtcttctg cgtagatccg tcgaagggtg gacgcaagcc ggcacgctta    480
atagtttacc cagacttggg cgtgcgggtc tgcgagaaga tggccctata cgacgtcacg    540
cagaagttac cacaggccgt gatgggttca gcatacggat tccagtactc ccccacccag    600
agggttgagt acctgctcaa aatgtggcgg tcaaagaagg tgcctatggg ctttctctac    660
gacaccaggt gttttgattc aaccgtcact gagcgggaca tccggactga aacgacatc     720
tatcagtctt gccagctgga tcccgtagca aggagggcag tatcatccct aacggaacgg    780
ctctacgtag cggccccat ggtgaactcc aagggacagt catgtggcta ccgtagatgc     840
cgagccagtg gggtgctgcc cacgagcatg gaaacacca tcacgtgcta tctgaaggca    900
caggccgcct gcagggcggc caacatcaag gactgtgaca tgttggtgtg cggagatgac    960
ttagtggtca tttgtgagag tgctggcgtc caggaggaca ctgagtcact gcagcattc    1020
acggatgcta tgaccaggta tcagctcccc ctggagacg ccccgcaacc tacttacgac    1080
cttgagctca taacatcatg ctcatccaat gtctccgtcg cccacgatgg caacgggaag    1140
agatattact acctcacacg tgactgtacc actccacttg cgcggccgc ctgggagaca    1200
gcccgccaca ctccagtcaa ctcgtggttg ggcaacatca ttatgtttgc ccccacgata    1260
tgggtgcgta tggttctgat gacccatttt ttctccatcc tccagtcaca agagcaattg    1320
gagaaagcac tcgactttga catctatgga gtgacctatt ccgtctctcc acttgatctc    1380
ccagcaatca ttcaacgact ccatggcatg gcagcatttt cactccacgg atactctcca    1440
gttgagctca atagggtagg ggcttgcctc aggaaacttg gggtgcctcc cttgcgagcc    1500
tggagacatc gagccagagc tgtcagagcc aaactcattg cccaagggg gaaagcggcc    1560
atatgcggta agtacctctt taactgggca gtgaagacca aactaaaact cactccattg    1620
gtctccgcga gcaagcttga cttatcaggc tggttcgtgg ccggctacga cgggggggac    1680
attttatcaca gcgtgtccca ggctcgaccc cgt                                1713
```

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11

```
ctccgtcgtg tgctgcgcca tgtc                                            24
```

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12

```
aaaaaaaaaa aaaaaaaaa aaaaaaaaaa aaaa                                  34
```

<210> SEQ ID NO 13
<211> LENGTH: 23
<212> TYPE: DNA
<213> ORGANISM: Artificial Sequence
<220> FEATURE:
<223> OTHER INFORMATION: Primer

```
<400> SEQUENCE: 13
tcatactctt ggaccggggc tct                                             23

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
gtgccgctct atcgagcggg gagt                                            24

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
atactcctgg acaggggccc t                                               21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
atactcctgg acaggggccc t                                               21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
ccgctctacc gagcgggag t                                                21

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
gagcgtggtc tgctgctcta tgtc                                            24

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
ataatatgat cacaccatgt agtgctgagg                                      30
```

```
<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ccagctcacc gtgctggcag g                                            21

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
gatcggagga cgtcgtgtgc tgtt                                         24

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
gttcgatgtc atactcgtgg actg                                         24

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
aagctgccta ccgagcaggc agca                                         24

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
ctaagctcag gctcttggtc cact                                         24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gacgacgtcg tatgttgttc catg                                         24

<210> SEQ ID NO 26
<211> LENGTH: 25
<212> TYPE: DNA
<213> ORGANISM: Artificial Sequence
<220> FEATURE:
<223> OTHER INFORMATION: Primer
```

```
-continued

<400> SEQUENCE: 26
ctaccgagcg gggagcaaaa agatg                                          25

<210> SEQ ID NO 27
<211> LENGTH: 8
<212> TYPE: PRT
<213> ORGANISM: Artificial Sequence
<220> FEATURE:
<223> OTHER INFORMATION: His-Tag

<400> SEQUENCE: 27

Leu Glu His His His His His His
 1               5

<210> SEQ ID NO 28
<211> LENGTH: 24
<212> TYPE: DNA
<213> ORGANISM: Artificial Sequence
<220> FEATURE:
<223> OTHER INFORMATION: Sequence encoding SEQ ID NO: 27

<400> SEQUENCE: 28
ctcgagcacc accaccacca ccac                                           24
```

HCV RNA-DEPENDENT RNA POLYMERASE

CROSS-REFERENCE TO RELATED APPLICATIONS

This application is a divisional of U.S. application Ser. No. 10/584,810, issued as U.S. Pat. No. 7,329,732, which is a 371 National Stage Application of PCT/US2005/000292, with an international filing date of Jan. 6, 2005, and claims the benefit of U.S. Provisional Application No. 60/535,708, filed Jan. 9, 2004.

BACKGROUND OF THE INVENTION

The references cited in the present application are not admitted to be prior art to the claimed invention.

It is estimated that about 3% of the world's population are infected with the Hepatitis C virus (HCV). (Wasley et al., 2000. *Semin. Liver Dis.* 20, 1-16.) Exposure to HCV results in an overt acute disease in a small percentage of cases, while in most instances the virus establishes a chronic infection causing liver inflammation and slowly progresses into liver failure and cirrhosis. (Iwarson, 1994. *FEMS Microbiol. Rev.* 14, 201-204.) Epidemiological surveys indicate HCV plays an important role in hepatocellular carcinoma pathogenesis. (Kew, 1994. *FEMS Microbiol. Rev.* 14, 211-220, Alter, 1995. *Blood* 85, 1681-1695.)

The HCV genome consists of a single strand RNA about 9.5 kb in length, encoding a precursor polyprotein about 3000 amino acids. (Choo et al., 1989. *Science* 244, 362-364, Choo et al., 1989. *Science* 244, 359-362, Takamizawa et al., 1991. *J. Virol.* 65, 1105-1113.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima et al., 1994. *J. Virol.* 68, 2731-2734, Hijikata et al., 1993. *Proc. Natl. Acad. Sci. USA* 90, 10773-10777.)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui et al., 1993. *J. Virol.* 67, 1385-1395, Hijikata et al., 1993. *Proc. Natl. Acad. Sci. USA* 90, 10773-10777.)

A distinct serine protease located in the N-terminal domain of NS3 is responsible for proteolytic cleavages at the NS3/NS4A, NS4A/NS4B, NS4B/NS5A and NS5A/NS5B junctions. (Barthenschlager et al., 1993. *J. Virol.* 67, 3835-3844, Grakoui et al., 1993. *Proc. Natl. Acad. Sci. USA* 90, 10583-10587, Tomei et al., 1993. *J. Virol.* 67, 4017-4026.) RNA stimulated NTPase and helicase activities are located in the C-terminal domain of NS3.

NS4A provides a cofactor for NS3 protease activity. (Failla et al., *J. Virol.* 1994. 68, 3753-3760, De Francesco et al., U.S. Pat. No. 5,739,002.)

NS5A is a highly phosphorylated protein conferring interferon resistance. (Pawlotsky 1999. *J. Viral Hepat. Suppl.* 1, 47-48.)

NS5B provides an RNA-dependent RNA polymerase. (De Francesco et al., International Publication Number WO 96/37619, published Nov. 28, 1996, Behrens et al., 1996. *EMBO* 15, 12-22, Lohmann et al., 1998. *Virology* 249, 108-118.) Soluble RNA-dependent RNA polymerase can be produced by a 21 amino acid truncation at the C terminus. (Yamashita et al., *The Journal of Biological Chemistry* 273: 15479-15486, 1998, Ferrari et al., *Journal of Virology* 73:1649-1654, 1999.)

Different genotypes and quasispecies of HCV have been identified. (Farci et al., *Seminars in Liver Disease* 20:103-126, 2000, Okamoto et al., *Virology* 188:331-341, 1992.)

SUMMARY OF THE INVENTION

The present invention features NS5B polypeptides from different clinically important HCV genotypes. The polypeptides can be used individually, or as part of a panel of RNA-dependent RNA polymerases, to evaluate the effectiveness of a compound to inhibit NS5B activity.

Thus, a first aspect of the present invention describes a purified polypeptide comprising an amino acid sequence selected from the group consisting of: SEQ ID NO: 1, SEQ ID NO: 2, SEQ ID NO: 3, SEQ ID NO: 4 and SEQ ID NO: 5. A "purified polypeptide" is present in an environment lacking one or more other polypeptides with which it is naturally associated and/or is represented by at least about 10% of the total protein present.

In different embodiments, the purified polypeptide represents at least about 50%, at least about 75%, or at least about 95% of the total protein in a sample or preparation. Reference to "purified polypeptide" does not require that the polypeptide has undergone any purification and may include, for example, chemically synthesized polypeptide that has not been purified.

Another aspect of the present invention describes a recombinant nucleic acid comprising a nucleotide sequence encoding an amino acid sequence selected from the group consisting of: SEQ ID NO: 1, SEQ ID NO: 2, SEQ ID NO: 3, SEQ ID NO: 4 and SEQ ID NO: 5. A recombinant nucleic acid is nucleic acid that by virtue of its sequence and/or form does not occur in nature. The form of the nucleic acid is provided by its association with other nucleic acids found in nature, such the absence of one or more other nucleic acid regions naturally associated with a particular nucleic acid (e.g., upstream or downstream regions) and/or purified nucleic acid.

Another aspect of the present invention describes a method of evaluating the ability of a compound to inhibit HCV RNA-dependent RNA polymerase. The method involves measuring the ability of the compound to inhibit the activity of one or more HCV RNA-dependent RNA polymerases having an amino acid sequence selected from the group consisting of SEQ ID NO: 1, SEQ ID NO: 2, SEQ ID NO: 3, SEQ ID NO: 4 and SEQ ID NO: 5.

Unless particular terms are mutually exclusive, reference to "or" indicates either or both possibilities. Occasionally phrases such as "and/or" are used to highlight either or both possibilities.

Reference to open-ended terms such as "comprises" allows for additional elements or steps. Occasionally phrases such as "one or more" are used with or without "comprises" to highlight the possibility of additional elements or steps.

Unless explicitly stated reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIGS. 1A-1E provide the amino acid sequence for different HCV NS5B sequences. FIG. 1A illustrates SEQ ID NO: 1, FIG. 1B illustrates SEQ ID NO: 2, FIG. 1C illustrates SEQ ID NO: 3, FIG. 1D illustrates SEQ ID NO: 4, and FIG. 1E illustrates SEQ ID NO: 5.

FIGS. 2A-2E provide nucleotide sequences encoding SEQ ID NO: 1-5. FIG. 2A (SEQ ID NO: 6) illustrates the nucleotide sequence encoding SEQ ID NO: 1. FIG. 2B (SEQ ID NO: 7) illustrates the nucleotide sequence encoding SEQ ID NO: 2. FIG. 2C (SEQ ID NO: 8) illustrates the nucleotide sequence encoding SEQ ID NO: 3. FIG. 2D (SEQ ID NO: 9) illustrates the nucleotide sequence encoding SEQ ID NO: 4. FIG. 2E (SEQ ID NO: 10) illustrates the nucleotide sequence encoding SEQ ID NO: 5.

DETAILED DESCRIPTION OF THE INVENTION

SEQ ID NOs: 1-5 provide NS5B sequences from different HCV genotypes. SEQ ID NO: 1 is from HCV genotype 2a. SEQ ID NO: 2 is from HCV genotype 2b. SEQ ID NO: 3 is from genotype 3a. SEQ ID NO: 4 is from genotype 4a. SEQ ID NO: 5 is from genotype 6a. SEQ ID NOs: 1-5 are all modified NS5B sequences containing an amino terminus methionine and a carboxyl terminus 21 amino acid deletion.

SEQ ID NOs: 1-5 provide polypeptides having RNA-dependent RNA polymerase activity. The polypeptides have different uses, such as providing RNA-dependent RNA polymerase activity based on different sequences and being used to evaluate the ability of a compound to inhibit HCV RNA-dependent RNA polymerase activity.

The polypeptides can be used individually, or as part of a panel of RNA-dependent RNA polymerases, to evaluate the effectiveness of a compound to inhibit HCV RNA-dependent RNA polymerase activity. Compounds affecting HCV NS5B activity have research and therapeutic applications. Research applications include using the compounds as a tool to study RNA-dependent RNA polymerases activity. Therapeutic applications include using those compounds having appropriate pharmacological properties such as efficacy and lack of unacceptable toxicity to treat or inhibit onset of HCV in a patient.

NS5B Sequences

NS5B sequences described herein include polypeptides containing a region structurally related to SEQ ID NOs: 1, 2, 3, 4 or 5. A polypeptide region "structurally related" to a reference polypeptide contains an amino acid identity of at least 90% to the reference polypeptide. Polypeptides containing a region structurally related to SEQ ID NOs: 1, 2, 3, 4 or 5 can also contain additional polypeptide regions that may or may not be related to NS5B.

Percent identity to a reference sequence is determined by aligning the polypeptide sequence with the reference sequence and determining the number of identical amino acids in the corresponding regions. This number is divided by the total number of amino acids in the reference sequence (e.g., SEQ ID NO: 1) and then multiplied by 100 and rounded to the nearest whole number.

Using SEQ ID NOs: 1, 2, 3, 4 or 5 as a frame of reference, alterations to the sequence can be made taking into account the known properties of amino acids. Alterations include one or more amino acid additions, deletions, and/or substitutions. The overall effect of different alterations can be evaluated using techniques described herein to confirm the ability of a particular polypeptide to provide RNA-dependent RNA polymerase activity.

Generally, in substituting different amino acids to retain activity it is preferable to exchange amino acids having similar properties. Factors that can be taken into account for an amino acid substitution include amino acid size, charge, polarity, and hydrophobicity. The effect of different amino acid R-groups on amino acid properties are well known in the art. (See, for example, Ausubel, *Current Protocols in Molecular Biology*, John Wiley, 1987-2002, Appendix 1C.)

In exchanging amino acids to maintain activity, the replacement amino acid should have one or more similar properties such as approximately the same charge and/or size and/or polarity and/or hydrophobicity. For example, substituting valine for leucine, arginine for lysine, and asparagine for glutamine are good candidates for not causing a change in polypeptide functioning.

Alterations to achieve a particular purpose include those designed to facilitate production or efficacy of the polypeptide; or cloning of the encoded nucleic acid. Polypeptide production can be facilitated through the use of an initiation codon (e.g., coding for methionine) suitable for recombinant expression. Cloning can be facilitated by, for example, the introduction of restriction sites which can be accompanied by amino acid additions or changes.

Additional regions can be added to, for example, facilitate polypeptide purification or identification. Examples of groups that can be used to facilitate purification or identification include polypeptides providing tags such as a six-histidine tag, trpE, glutathione and maltose-binding protein.

In different embodiments, the SEQ ID NOs: 1, 2, 3, 4 or 5 polypeptide comprises, consists essentially, or consists, of a sequence at 90%, at least 95%, or at least 99% identical to SEQ ID NOs: 1, 2, 3, 4 or 5; or differing from SEQ ID NOs: 1, 2, 3, 4 or 5 by 0, 1, 2, 3, 4, 5, 6, 7, 8, 9, 10, 11, 12, 13, 14, 15, 16, 17, 18, or 19 amino acid alterations.

Polypeptide Production and Purification

Polypeptides can be produced using standard techniques including those involving chemical synthesis and those involving purification from a cell producing the polypeptide. Techniques for chemical synthesis of polypeptides are well known in the art. (See e.g., Vincent, *Peptide and Protein Drug Delivery*, New York, N.Y., Decker, 1990.)

Obtaining polypeptides from a cell is facilitated using recombinant nucleic acid techniques to produce the polypeptide. Recombinant nucleic acid techniques for producing a polypeptide involve introducing, or producing, a recombinant gene encoding the polypeptide in a cell and expressing the polypeptide.

A recombinant gene contains nucleic acid encoding a polypeptide along with regulatory elements for polypeptide expression. The recombinant gene can be present in a cellular genome or can be part of an expression vector.

The regulatory elements that may be present as part of a recombinant gene include those naturally associated with the polypeptide encoding sequence and exogenous regulatory elements not naturally associated with the polypeptide encoding sequence. Exogenous regulatory elements such as an exogenous promoter can be useful for expressing a recombinant gene in a particular host or increasing the level of expression. Generally, the regulatory elements that are present in a recombinant gene include a transcriptional promoter, a ribosome binding site, a terminator, and an optionally present operator.

Expression of a recombinant gene in a cell is facilitated through the use of an expression vector. Preferably, an expression vector in addition to a recombinant gene also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Due to the degeneracy of the genetic code, a large number of different encoding nucleic acid sequences can be used to code for a particular polypeptide. The degeneracy of the genetic code arises because almost all amino acids are encoded by different combinations of nucleotide triplets or "codons". Amino acids are encoded by codons as follows:

```
A = Ala = Alanine:        codons GCA, GCC, GCG, GCU

C = Cys = Cysteine:       codons UGC, UGU

D = Asp = Aspartic acid:  codons GAC, GAU

E = Glu = Glutamic acid:  codons GAA, GAG

F = Phe = Phenylalanine:  codons UUC, UUU

G = Gly = Glycine:        codons GGA, GGC, GGG, GGU

H = His = Histidine:      codons CAC, CAU

I = Ile = Isoleucine:     codons AUA, AUC, AUU

K = Lys = Lysine:         codons AAA, AAG

L = Leu = Leucine:        codons UUA, UUG, CUA, CUC,
                                 CUG, CUU M = Met = Methionine:     codon AUG N = Asn = Asparagine:     codons AAC, AAU P = Pro = Proline:        codons CCA, CCC, CCG, CCU Q = Gln = Glutamine:      codons CAA, CAG R = Arg = Arginine:       codons AGA, AGG, CGA, CGC,
                                 CGG, CGU S = Ser = Serine:         codons AGC, AGU, UCA, UCC,
                                 UCG, UCU T = Thr = Threonine:      codons ACA, ACC, ACG, ACU V = Val = Valine:         codons GUA, GUC, GUG, GUU W = Trp = Tryptophan:     codon UGG Y = Tyr = Tyrosine:       codons UAC, UAU
```

Techniques for recombinant gene production, introduction into a cell, and recombinant gene expression are well known in the art. Examples of such general techniques are provided in references such as Ausubel, *Current Protocols in Molecular Biology*, John Wiley, 1987-2002, and Sambrook et al., *Molecular Cloning, A Laboratory Manual*, 2$^{nd}$ Edition, Cold Spring Harbor Laboratory Press, 1989.

Methods applying recombinant gene production to HCV RNA-dependent RNA polymerase expression are described in the scientific literature and the Examples provided below. The purification of full-length enzyme from insect cells transfected with a baculoviral vector has been described. (Lohmann et al, *J. Virol.* 71:8416-8428, 1997; De Francesco et al., *Meth. Enzymol.* 275: 58-67, 1996). The full length enzyme has also been purified from *E. coli*. (Oh et al, *J. Virol.* 73:7694-76702, 1999).

The C-terminal region of the HCV RNA polymerase contains a stretch of highly hydrophobic amino acids that decrease the solubility of the enzyme in the absence of detergent and likely serve as a membrane anchor in vivo. Forms of the HCV RNA polymerase with the C-terminus truncated to remove these hydrophobic amino acids have been expressed in and purified from *E. coli* using conventional column chromatography. (Yamashita et al, *J. Biol. Chem.* 273:15479-15486, 1998; Ferrari et al., *J. Virol.* 73:1649-1654, 1999; Carroll et al., *Biochemistry* 39: 8243-8249, 2000; Luo et al., *J. Virol* 74:851-63, 2000; Leveque et al., *J. Virol.* 77:9020-9028, 2003.)

NS5B Assays

Techniques for measuring HCV RNA-dependent RNA polymerase activity are well known in the art. Examples of techniques for measuring HCV RNA-dependent RNA polymerase activity are provided in the references cited in the prior section concerning HCV expression and purification.

EXAMPLES

Examples are provided below further illustrating different features of the present invention. The examples also illustrate useful methodology for practicing the invention. These examples do not limit the claimed invention.

Example 1

Rescue and Characterization of NS5B

NS5B genes were rescued and characterized from the sera of chronically infected chimpanzees. Total RNA was isolated from serum samples of chimpanzees chronically infected with HCV using an RNA purification kit (QIAGEN RNEASY MINI KIT) according to manufacturer's instructions (QIAGEN, Inc. Valencia, Calif.). Total RNA (5 to 10 microliters) was used as a template for the reverse transcriptase reaction (using SUPERSCRIPT II RT reverse transcriptase, Invitrogen Life Technologies, Carlsbad, Calif.) with a 34 nucleotide dATP primer. RT reactions were heat inactivated at 65° C. for 15 minutes, and then digested with 1 μL each RNAseH and RNAseT1 (Roche Applied Science, Indianapolis, Ind.) at 37° C. for 20 minutes to remove RNA prior to PCR. Nested PCR was performed using a blend of enzymes consisting of Taq DNA Polymerase and the Tgo DNA Polymerase proofreading enzyme (EXPAND HIGH FIDELITY PCR SYSTEM from Roche Applied Science, Indianapolis, Ind.) and the following primers:

```
Genotype 2a
PCR1, forward
5'-CTCCGTCGTGTGCTGCGCCATGTC         (SEQ ID NO: 11)

reverse 34 nucleotide dATP          (SEQ ID NO: 12)

PCR2, forward
5'TCATACTCTTGGACCGGGGCTCT           (SEQ ID NO: 13)

reverse
5'GTGCCGCTCTATCGAGCGGGGAGT          (SEQ ID NO: 14)

Genotype 2b
PCR1, forward
5'-ATACTCCTGGACAGGGGCCCT            (SEQ ID NO: 15)

reverse 34 nucleotide dATP          (SEQ ID NO: 12)
```

```
                            -continued
PCR2, forward
5'ATACTCCTGGACAGGGGCCCT              (SEQ ID NO: 16)

reverse
5'CCGCTCTACCGAGCGGGAGT               (SEQ ID NO: 17)

Genotype 3a
PCR1, forward
5'-GAGCGTGGTCTGCTGCTCTATGTC          (SEQ ID NO: 18)

reverse 5'-34 nucleotide dATP        (SEQ ID NO: 12)

PCR2, forward
5'-ATAATATGATCACACCATGTAGTGCTGAGG    (SEQ ID NO: 19)

reverse
5'-CCAGCTCACCGTGCTGGCAGG             (SEQ ID NO: 20)

Genotype 4a
PCR1, forward
5'-GATCGGAGGACGTCGTGTGCTGTT          (SEQ ID NO: 21)

reverse 5'-34 nucleotide dATP        (SEQ ID NO: 12)

PCR2, forward
5'-GTTCGATGTCATACTCGTGGACTG          (SEQ ID NO: 22)

reverse
5'-AAGCTGCCTACCGAGCAGGCAGCA          (SEQ ID NO: 23)

Genotype 6a
PCR1, forward
5'-CTAAGCTCAGGCTCTTGGTCCACT          (SEQ ID NO: 24)

reverse 5'-34 nucleotide dATP        (SEQ ID NO: 12)

PCR2, forward
5'-GACGACGTCGTATGTTGTTCCATG          (SEQ ID NO: 25)

reverse
5'-CTACCGAGCGGGGAGCAAAAAGATG         (SEQ ID NO: 26)
```

PCR products were cloned into pGEM-T and individual clones sequenced. Genotype was confirmed based upon closest homology to prototype sequences listed in GenBank.

Example 2

Construction of NS5B Expression Clones

The BK NS5B Δ21 gene (Carroll et al., *J. Biol. Chem.* 278:11979-11984, 2003) was modified by standard molecular biology techniques to encode the sequence Leu-Glu-His-His-His-His-His-His (SEQ ID NO: 27) (CTCGAGCACCACCACCACCACCAC SEQ ID NO: 28) at the C-terminal end of the NS5B Δ21 coding sequence after codon 570, and then followed by a stop codon. The Leu-Glu pair is encoded by a unique XhoI site that is just in front of the histidine tag. The vector was further modified to encode a unique BclI sites at NS5B codon 10. This vector served as a template to subclone additional NS5B genes for protein expression as BclI-Xho fragments.

SEQ ID NOs: 1-5 all initiate with the first 10 codons of genotype 1b BK sequences. NS5B genes were cloned in frame as BclI-XhoI fragments using clone specific PCR primers. The NS5B constructs lacked the C-terminal 21 residues, which previously was demonstrated to increase solubility. All constructs were verified by DNA sequencing.

Example 3

Bacterial Expression of NS5B Δ21 Enzymes

Glycerol stocks were used as seed cultures for large-scale purification. Glycerol stocks were prepared by transforming DNA into competent cells (ROSETTA DE3 cells) (Novagen). A 20 mL overnight culture of Luria-Bertani (LB) broth (containing 50 μg/mL ampicillin, 34 μg/mL chloramphemcol) was inoculated from a single colony. Cells were collected by centrifugation and used to inoculate a 1 L culture of LB broth with 100 μg/mL ampicillin only, and grown to mid-log phase ($A_{600}$ of 0.4-0.5). To generate glycerol stocks, cells were again collected by centrifugation and resuspended, per liter of culture, in 50 mL ice cold LB broth. Then 500 μl aliquots of cells were individually mixed with 500 μl of 50% glycerol, placed into storage vials, quick frozen on dry ice and kept at −70° C. until use.

For large-scale growth, a glycerol stock was plated on LB plates containing 50 μg/mL ampicillin and 34 μg/mL chloramphenicol (Teknova), incubated overnight at 37° C., collected through scraping, and used as an inoculum for a 200 mL starter culture. After ~15 minutes of shaking at 225 rpm at 37° C., 20 mL of the starter culture was used to seed 980 mL of LB broth containing 100 μg/mL ampicillin. The cultures were grown to an optical density of $A_{600}$ nm of ~0.7, and induced with 1 mM of isopropylthio-β-galactoside (IPTG from Invitrogen Life Technologies Inc.). The temperature and shaking were then lowered to 18° C. and 210 rpm for the 18 hour induction period. Cells were collected by centrifugation and stored at −70° C. until use.

Example 4

Purification of NS5B Δ21

All steps in the purification were performed on ice or in a refrigerated 4° C. cold room, and with pre-chilled buffers. Cell pellets were resuspended with 200 mL of lysis buffer (20 mM Tris-HCl pH 7.5, 10% glycerol, 0.5 M KCl, 5 mM $MgCl_2$, 2 mM β-mercaptoethanol (β-ME), 0.2% n-octylglucoside, Complete EDTA-Free Protease Inhibitors from Roche Diagnostics Corp.). To this was added 5,000 U DNase I (grade I, Roche) and incubated with stirring for 10 minutes. This mixture was dounce homogenized until the lysate was homogenous, then fluidized with three passes thru a high pressure fluids processor (MICROFLULDIZER® model 110Y, Microfluidics Corporation). The fluidized lysate was centrifuged at 15,000 rpm for 30 minutes in a JA-17 rotor (Beckman Coulter).

The supernatant was collected, mixed with 5 mL of packed Cobalt affinity resin (TALON® CellThru resin from (Clontech), and incubated for 1 hour with gentle agitation to allow sample binding. The mixture was centrifuged at 1750 rpm in the GH-3.8 rotor (Beckman Coulter) for 5 minutes to pellet the resin. The protein-bound resin was washed with 5 column volumes of Wash-EQ buffer (20 mM Tris-HCl pH 7.5, 10% glycerol, 0.5 M KCl, 2 mM βME, 0.2% n-octylglucoside) for 5 minutes, the resin pelleted by centrifugation at 1750 rpm in the GH-3.8 rotor for 2 minutes, and the supernatant removed. This wash procedure was repeated an additional four times. The resin was then washed a final time with 5 column volumes of Wash buffer (20 mM Tris-HCl pH 7.5, 10% glycerol, 0.5 M KCl, 2 mM βME, 0.2% n-octylglucoside, 10 mM Imidazole).

To elute protein, the resin was resuspended with 1 column volume of elution buffer (20 mM Tris-HCl pH 7.5, 10% glycerol, 0.5 M KCl, 2 mM β-ME, 0.2% n-octylglucoside, 200 mM Imidazole) and incubated with gentle agitation for 10 minutes. The resin was pelleted by centrifugation at 1750 rpm in the GH-3.8 rotor for 2 minutes, the eluate collected, and EDTA added to a final concentration of 1 mM. The elution procedure was repeated twice more, but the eluates were kept separate. The eluates were then dialyzed in dialysis buffer (20 mM Tris-HCl pH 7.5, 10% glycerol, 0.5 M KCl, 3 mM dithiothreitol (DTT), 0.2% n-octylglucoside) with a change of buffer. Concentrated eluate fractions (>50% of the most concentrated fraction) were combined, aliquoted, quick frozen on dry ice, and stored enzyme at −70° C. until use.

Protein quantitation was performed using Pierce's Coomassie Plus Protein reagent and a microplate reader (MOLECULAR DEVICES SPECTRA MAX 250 with the SOFTMAXPRO v3.1.1 data acquisition and analysis software). Protein visualization was performed using 4-15% gradient Tris-HCl SDS PAGE gels (Bio-Rad) and Bio-Safe Coomassie (Bio-rad). Protein purity was determined by quantitation using a phosphoimager (the STORM860 with IMAGEQUANT quantization software from Molecular Dynamics).

Example 5

Polymerase Assay

The genotype 2a (SEQ ID NO: 1), 2b (SEQ ID NO: 2), and 3a (SEQ ID NO: 3) polymerases were titrated in activity-linearity assays in a final concentration range between 62.5 nM to 1500 nM (1250 nM for the SEQ ID NO: 3 enzyme). Polymerase was pre-incubated for 1 hour at room temperature with 0.75 µg per reaction of t500 RNA template (IBA GMBH) in a volume of 45 µl. t500 RNA template is comprised of bases 3504-4004 of the HCV BK genome and corresponds to the NS2/3 region as previously described (Carroll et al., *Biochemistry* 39:8243-8249, 2000). The following final buffer conditions were: 20 mM Tris-HCl pH 7.5; 50 µM EDTA; 5 mM DTT; 2 mM MgCl$_2$; 80 mM KCl; 0.4 U/µL rRNAsin (Promega).

The reaction was initiated by the addition of 5 µl of a nucleotide triphosphate cocktail which consisted of 10 µM each ATP, CTP, UTP, and GTP (Ultrapure NTP set from Amersham Biosciences) which had been spiked with 0.2 µl of α$^{33}$P GTP (10 mCi/ml, Perkin Elmer Life Sciences). Assay conditions for genotype 4a (SEQ ID NO: 4) and 6a (SEQ ID NO: 5) enzymes were identical to that described for SEQ ID NOs: 1-3 except that the nucleotide concentrations were 100 µM each. The final enzyme reaction volume was 50 µl. To quench the reaction, 20 µL of 0.5 M EDTA was added. For quantitation, 50 µL of the quenched reaction was blotted onto DE81 Whatman filter disks, dried, washed ten times with 200 mL of 0.3 M ammonium formate pH 8.0, ethanol rinsed, dried, imaged with Storm860/ImageQuant, and quantitated by liquid scintillation counting. The results are shown in Tables 1 and 2. By way of comparison, a Δ21 histidine tagged HCV BK NS5B purified and assayed under similar conditions had a specific activity of 74 nmol/ hr*mg.

TABLE 1

| SEQ ID NO: | Specific Activity [nmol/(hr*mg)] |
|---|---|
| 1 | 2 |
| 2 | 15 |
| 3 | 147 |

TABLE 2

| SEQ ID NO: | Specific Activity [nmol/(hr*mg)] |
|---|---|
| 4 | 2 |
| 5 | 2 |

Other embodiments are within the following claims. While several embodiments have been shown and described, various modifications may be made without departing from the spirit and scope of the present invention.

What is claimed is:
1. A purified polypeptide comprising SEQ ID NO: 3.
2. The polypeptide of claim 1, wherein said polypeptide consists of the amino acid sequence of SEQ ID NO:3.

* * * * *